(12) United States Patent
Krasniak et al.

(10) Patent No.: US 12,295,591 B2
(45) Date of Patent: May 13, 2025

(54) BONE PUNCH INSTRUMENT

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Carolyn M. Krasniak, Melrose, MA (US); Cori G. Pierce, Salem, NH (US); Kevin M. Falco, Chelmsford, MA (US); Jeffrey L. Barnes, Medford, MA (US)

(73) Assignees: Smith & Nephew, Inc., Zug (SG); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 332 days.

(21) Appl. No.: 17/899,253

(22) Filed: Aug. 30, 2022

(65) Prior Publication Data
US 2022/0409212 A1 Dec. 29, 2022

Related U.S. Application Data

(63) Continuation of application No. PCT/US2021/023011, filed on Mar. 18, 2021.
(Continued)

(51) Int. Cl.
*A61B 17/16* (2006.01)
*A61B 17/06* (2006.01)

(52) U.S. Cl.
CPC .... *A61B 17/1604* (2013.01); *A61B 17/06066* (2013.01)

(58) Field of Classification Search
CPC .................................................. A61B 17/1604
See application file for complete search history.

(56) References Cited

U.S. PATENT DOCUMENTS

| 3,955,581 A | 5/1976 | Spasiano et al. |
|---|---|---|
| 6,436,110 B2 | 8/2002 | Bowman et al. |
| (Continued) | | |

FOREIGN PATENT DOCUMENTS

EP 2732776 A1 5/2014

OTHER PUBLICATIONS

International Search Report and Written Opinion for International Application PCT/US2021/023011 mailed Jun. 21, 2021.

*Primary Examiner* — Larry E Waggle, Jr.
(74) *Attorney, Agent, or Firm* — Seager, Tufte & Wickhem LLP

(57) ABSTRACT

A medical device configured to form one or more holes within a bone of a patient may include a handle assembly including a housing, a lever rotatably coupled to the housing, and a sheath extending distally from the housing, the handle assembly including a spring biasing the lever toward an initial or intermediate position; and a bone punch including an elongate shaft, a head at a proximal end of the elongate shaft, and a piercing tip at a distal end of the elongate shaft configured to be driven into the bone. The elongate shaft may be slidably disposed within the sheath in a first position when the lever is in the initial or intermediate position. Translation of the bone punch distally within the sheath from the first position to a second position may cause a distal end of the lever to rotate away from the housing to an extended position.

19 Claims, 27 Drawing Sheets

Related U.S. Application Data

(60) Provisional application No. 63/091,107, filed on Oct. 13, 2020, provisional application No. 62/991,993, filed on Mar. 19, 2020.

(56) References Cited

U.S. PATENT DOCUMENTS

| | | |
|---|---|---|
| 7,083,075 B2 | 8/2006 | Swayze et al. |
| 7,189,243 B1 | 3/2007 | Seelig et al. |
| 8,821,531 B2 | 9/2014 | Miyamoto |
| 8,894,669 B2 | 11/2014 | Nering et al. |
| 8,906,025 B2 * | 12/2014 | Yoko ................. A61B 17/1604 606/88 |
| 9,370,356 B2 | 6/2016 | Euteneuer et al. |
| 9,532,814 B2 | 1/2017 | Harper |
| 9,763,659 B2 | 9/2017 | Sholev et al. |
| 10,758,228 B2 | 9/2020 | Zenz-Olson et al. |
| 2013/0144350 A1 | 6/2013 | Yoko et al. |
| 2016/0120538 A1 * | 5/2016 | Westling ............ A61B 17/0642 606/151 |
| 2018/0125474 A1 | 5/2018 | Dougherty et al. |
| 2018/0242983 A1 | 8/2018 | Rosner et al. |

\* cited by examiner

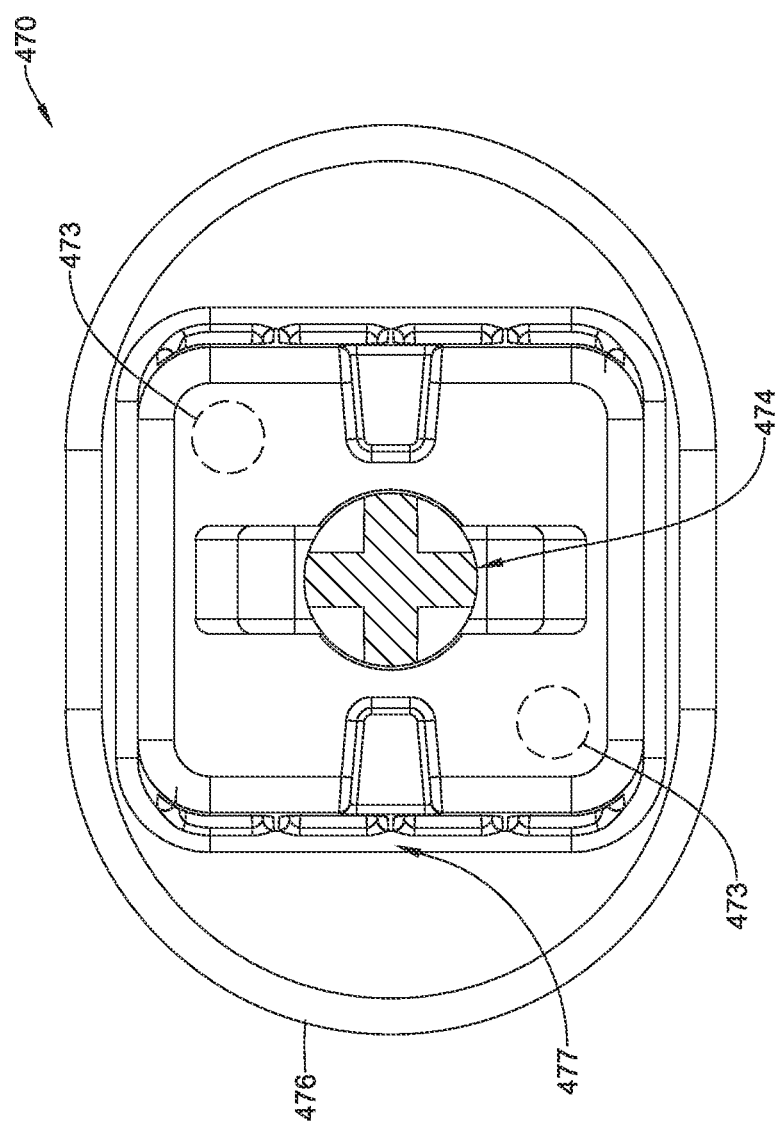

BONE PUNCH INSTRUMENT

CROSS REFERENCE TO RELATED APPLICATIONS

This application is a continuation of International Application No. PCT/US2021/023011, filed Mar. 18, 2021, titled BONE PUNCH INSTRUMENT, which claims the benefit of and priority to US Provisional Patent Application Ser. No. 62/991,993, filed on Mar. 19, 2020, titled BONE PUNCH INSTRUMENT, and US Provisional Patent Application Ser. No. 63/091,107, filed on Oct. 13, 2020, titled BONE PUNCH INSTRUMENT, the disclosures of which are incorporated herein by reference.

TECHNICAL FIELD

The present disclosure pertains generally to medical devices, and methods for manufacturing and/or using medical devices. More particularly, the present disclosure pertains to devices for making an aperture in bone within patients, and methods for manufacturing and using such devices.

BACKGROUND

Injuries may require the placement of anchors and/or implants into the bone(s) of a patient to repair. In one example, injuries to tendons may be treated by affixing a tendon repair implant to one or more bones associated with an articulating joint, such as the glenohumeral joint. Such affixation may use an anchor member, such as a staple, or other securement element inserted at least partially into bone, and in some cases, inserted at least partially into holes formed in the bone to receive the anchor member, staple, or other securement element. Formation of these holes and subsequent removal of a tool for doing so may be difficult due to the cortical elasticity of the bone. Of the known medical devices, and methods of manufacturing and using those devices, each has certain advantages and disadvantages. There is an ongoing need for improved and/or alternative medical devices and methods of making and using such devices.

SUMMARY

In one example, a medical device configured to form one or more holes within a bone of a patient may comprise a handle assembly including a housing, a lever rotatably coupled to the housing between an initial position and an extended position, and a sheath extending distally from the housing; and a bone punch including an elongate shaft, a head at a proximal end of the elongate shaft, and a piercing tip at a distal end of the elongate shaft, wherein the piercing tip is configured to be driven into the bone. The elongate shaft may be slidably disposed within the sheath in a first position when the lever is in the initial position. Translation of the bone punch distally within the sheath from the first position to a second position may cause a distal end of the lever to rotate away from the housing to the extended position.

In addition or alternatively to any example disclosed herein, the head of the bone punch is releasably engaged with the housing in the first position.

In addition or alternatively to any example disclosed herein, a distal surface of the head of the bone punch engages a proximal surface of the housing in the second position.

In addition or alternatively to any example disclosed herein, less than 40% of the piercing tip extends distally of the sheath in the first position.

In addition or alternatively to any example disclosed herein, translation of the bone punch distally within the sheath from the first position to the second position causes the distal end of the lever to rotate away from a longitudinal axis of the bone punch.

In addition or alternatively to any example disclosed herein, a distal end of the sheath is configured to be disposed adjacent a surface of the bone. A rotational position of the lever relative to the housing may indicate a depth of the piercing tip within the bone.

In addition or alternatively to any example disclosed herein, rotation of the lever from the extended position toward the initial position generates proximal translation of the bone punch to extract the piercing tip from the bone.

In addition or alternatively to any example disclosed herein, the handle assembly includes a spring biasing the lever toward the initial position.

In a second example, a medical device configured to form one or more holes within a bone of a patient may comprise: a handle assembly including a housing, a lever rotatably coupled to the housing between an initial position and an extended position, and a sheath extending distally from the housing; and a bone punch including an elongate shaft, a head at a proximal end of the elongate shaft, and a piercing tip at a distal end of the elongate shaft, wherein the piercing tip is configured to be driven into the bone. The elongate shaft may be slidably disposed within the sheath in a first position when the lever is in the initial position. The handle assembly may include a linkage disposed within the housing. The head of the bone punch may engage the linkage in the first position and distal translation of the bone punch from the first position to a second position may cause the linkage to rotate a distal end of the lever away from the housing to the extended position.

In addition or alternatively to any example disclosed herein, the linkage includes an ejector block slidably disposed within the housing.

In addition or alternatively to any example disclosed herein, the linkage further includes a distal link pivotably engaged with the housing at a distal pivot point and a middle link pivotably engaged with the ejector block at a proximal pivot point.

In addition or alternatively to any example disclosed herein, the distal link is pivotably engaged with the middle link at an intermediate pivot point between the distal pivot point and the proximal pivot point.

In addition or alternatively to any example disclosed herein, the distal link includes a cam surface configured to engage the lever.

In addition or alternatively to any example disclosed herein, distal translation of the head of the bone punch from the first position to the second position translates the ejector block distally within the housing.

In addition or alternatively to any example disclosed herein, rotation of the lever toward a longitudinal axis of the bone punch when the bone punch is in the second position actuates the linkage to translate the head of the bone punch proximally to extract the piercing tip from the bone.

In addition or alternatively to any example disclosed herein, the handle assembly includes a spring biasing the lever toward the initial position.

In a third example, a medical device configured to form one or more holes within a bone of a patient may comprise: a handle assembly including a housing, a lever rotatably coupled to the housing between an initial position and an extended position, and a sheath extending distally from the housing; and a bone punch including an elongate shaft having gear teeth extending outwardly therefrom, a head at a proximal end of the elongate shaft, and a piercing tip at a distal end of the elongate shaft, wherein the piercing tip is configured to be driven into the bone. The elongate shaft may be slidably disposed within the sheath in a first position when the lever is in the initial position. The handle assembly may include a plurality of gears disposed within the housing, at least one of the plurality of gears being configured to engage with the gear teeth of the elongate shaft. The head of the bone punch may be spaced away from a proximal surface of the housing in the first position and distal translation of the bone punch from the first position to a second position may cause the plurality of gears to rotate a distal end of the lever away from the housing to the extended position.

In addition or alternatively to any example disclosed herein, in the initial position, the lever is engaged with an outer surface of the housing.

In addition or alternatively to any example disclosed herein, in the initial position, the lever extends toward a distal end of the sheath generally parallel to a longitudinal axis of the sheath.

In addition or alternatively to any example disclosed herein, in the extended position, the lever extends toward a distal end of the sheath at an oblique angle to the sheath.

In addition or alternatively to any example disclosed herein, in the second position, a distal surface of the head of the bone punch is engaged with a proximal surface of the housing.

In addition or alternatively to any example disclosed herein, the plurality of gears includes a first gear configured to engage the gear teeth of the elongate shaft, a second gear fixedly secured to the lever, and a third gear engaged with both the first gear and the second gear.

In a fourth example, a medical device configured to form one or more holes within a bone of a patient may comprise: a handle assembly including a housing, a lever rotatably coupled to the housing between an initial position and an extended position, and a sheath extending distally from the housing; and a bone punch including an elongate shaft, a head at a proximal end of the elongate shaft, and a piercing tip at a distal end of the elongate shaft, wherein the piercing tip is configured to be driven into the bone. The elongate shaft may be slidably disposed within the sheath in a first position when the lever is in the initial position. The handle assembly may include a linkage disposed within the housing, the linkage including an ejector block slidably disposed within the housing. The head of the bone punch may be releasably coupled to the ejector block in the first position, and distal translation of the bone punch from the first position to a second position may cause the linkage to rotate a distal end of the lever away from the housing to the extended position.

In addition or alternatively to any example disclosed herein, the head of the bone punch is magnetically coupled to the ejector block.

In addition or alternatively to any example disclosed herein, the head of the bone punch includes one or more magnets disposed therein and the ejector block includes a magnetic material disposed therein opposite the one or more magnets.

In addition or alternatively to any example disclosed herein, the ejector block includes one or more magnets disposed therein and the head of the bone punch includes a magnetic material disposed therein opposite the one or more magnets.

In addition or alternatively to any example disclosed herein, the head of the bone punch includes one or more magnets disposed therein and the ejector block includes one or more magnets disposed therein opposite the one or more magnets disposed in the head of the bone punch.

In addition or alternatively to any example disclosed herein, distal translation of the head of the bone punch from the first position to the second position translates the ejector block distally within the housing.

In addition or alternatively to any example disclosed herein, rotation of the lever from the extended position toward a longitudinal axis of the bone punch when the bone punch is in the second position generates proximal translation of the bone punch to extract the piercing tip from the bone.

In addition or alternatively to any example disclosed herein, at least a portion of the head of the bone punch is configured to pass through an opening in a wall of the housing as the bone punch is translated from the first position to the second position.

The above summary of some embodiments, aspects, and/or examples is not intended to describe each disclosed embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description in connection with the accompanying drawings, in which:

FIG. 19A is a view of the head of the bone punch taken along line 19A-19A of FIG. 19;

Figure 1:
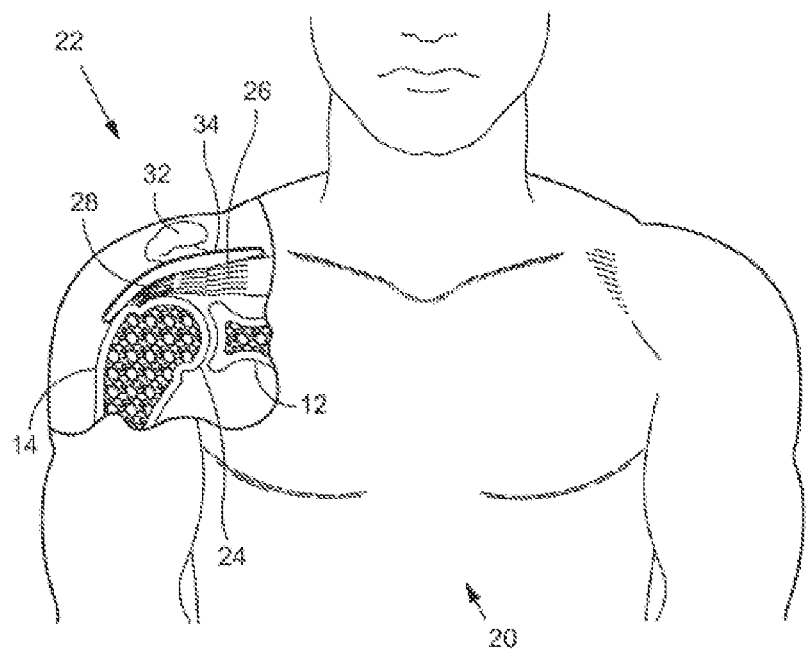
FIG. 1 is a stylized anterior view of a shoulder including a humerus and a scapula.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in to each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc. The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together, particularly where those discrete structures or elements remain individually identifiable.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures generally illustrate selected components and/or arrangements of medical devices or instruments. It should be noted that in any given figure, some features of the medical devices or instruments may not be shown, or may be shown schematically, for simplicity. Additional details regarding some of the elements of the medical devices or instruments may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to features or elements may be equally referred to all instances and quantities beyond one of said feature or element. As such, it will be understood that the following discussion may apply equally to any and/or all of the elements for which there are more than one within the medical devices or instruments, unless explicitly stated to the contrary. Additionally, not all instances of some elements or features may be shown in each figure for clarity.

FIG. 1 is a stylized anterior view of a patient 20 illustrating one example area that may benefit from the disclosed invention. For purposes of illustration, a shoulder 22 of patient 20 is shown in partial cross-section in FIG. 1. The shoulder 22 includes a humerus 14 and a scapula 12. In FIG. 1, a head 24 of the humerus 14 can be seen mating with a glenoid fossa of the scapula 12 at a glenohumeral joint. With reference to FIG. 1, it will be appreciated that the glenoid fossa comprises a shallow depression in the scapula 12. Movement of the humerus 14 relative to the scapula 12 is controlled by a number of muscles including: the deltoid, the supraspinatus, the infraspinatus, the subscapularis, and the teres minor. For purposes of illustration, only the supraspinatus 26 is shown in FIG. 1.

In FIG. 1, a distal tendon 28 of the supraspinatus 26 meets the humerus 14 at an insertion point. The scapula 12 of the shoulder 22 includes an acromion 32. In FIG. 1, a subacromial bursa 34 is shown extending between the acromion 32 of the scapula 12 and the head 24 of the humerus 14. The subacromial bursa 34 is shown overlaying the supraspinatus 26 as well as the distal tendon 28 and a portion of the humerus 14. The subacromial bursa 34 is one of the hundreds of bursae found the human body. Each bursa comprises a fluid filled sac. The presence of these bursae in the body reduces friction between bodily tissues.

Figure 2:
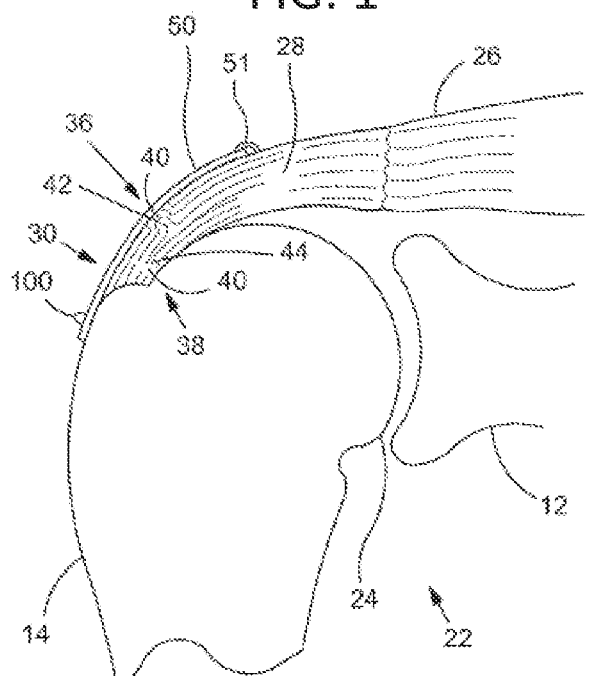
FIG. 2 is a stylized anterior view of a shoulder depicting the head of the humerus shown mating with the glenoid fossa of the scapula at a glenohumeral joint and a sheet-like material is affixed to the tendon.

The exemplary staples or fasteners described herein may be used to affix tendon repair implants to various target tissues in one example use of the disclosed medical device(s). The shoulder 22 depicted in FIG. 1 is one example where a tendon repair implant may be affixed to one or more bones associated with an articulating joint, such as the glenohumeral joint. Additionally, the tendon repair implant may be affixed to one or more tendons to be treated. In some cases, the tendons to be treated may be torn, partially torn, have internal micro-tears, be untorn, and/or be thinned due to age, injury or overuse. FIG. 2 is a stylized anterior view of the shoulder 22 including the humerus 14 and the scapula 12. In FIG. 2, the head 24 of the humerus 14 is shown mating with the glenoid fossa of the scapula 12 at the glenohumeral joint. The supraspinatus 26 is also shown in FIG. 2. This muscle, along with others, controls the movement of the humerus 14 relative to the scapula 12. The distal tendon 28 of the supraspinatus 26 meets the humerus 14 at an insertion point 30.

As depicted in FIG. 2, the distal tendon 28 may include a first damaged portion 36. A number of loose tendon fibers 40 in the first damaged portion 36 are visible in FIG. 2. The first damaged portion 36 includes a first tear 42 extending partially through the distal tendon 28. The first tear 42 may therefore be referred to as a partial thickness tear. In FIG. 2, the first tear 42 begins on the side of the distal tendon 28 facing the subacromial bursa (e.g., FIG. 1) and ends midway through the distal tendon 28. Accordingly, the first tear 42 may be referred to as a bursal side tear.

In FIG. 2, the distal tendon 28 also includes a second damaged portion 38 located near insertion point 30. As illustrated, the second damaged portion 38 of the distal tendon 28 has become frayed and a number of loose tendon fibers 40 are visible. The second damaged portion 38 of the distal tendon 28 includes a second tear 44. The second tear 44 begins on the side of the distal tendon 28 facing the center of the head 24 of the humerus 14. Accordingly, the second damaged portion 38 may be referred to as an articular side tear.

FIG. 2 illustrates a sheet-like implant 50 has been placed over the bursal side of the distal tendon 28. The sheet-like implant 50 may be affixed to the distal tendon 28 by a plurality of tendon staples 51. The sheet-like implant 50 may be affixed to the humerus 14 by one or more bone staples 100, or other similar and/or suitable bone anchors. The sheet-like implant 50 extends over the insertion point 30, the first tear 42, and the second tear 44. Some methods in accordance with this disclosure may include placing a tendon repair implant on the bursal side of a tendon regardless of whether the tears being treated are on the bursal side, the articular side, or within the tendon. In some cases, the exact location and nature of the tears being treated may be unknown. In some cases, the tendon repair implant may be applied to the bursal side of the tendon to treat shoulder pain that is most likely caused by one or more partial thickness tears in the tendon.

Figure 3:
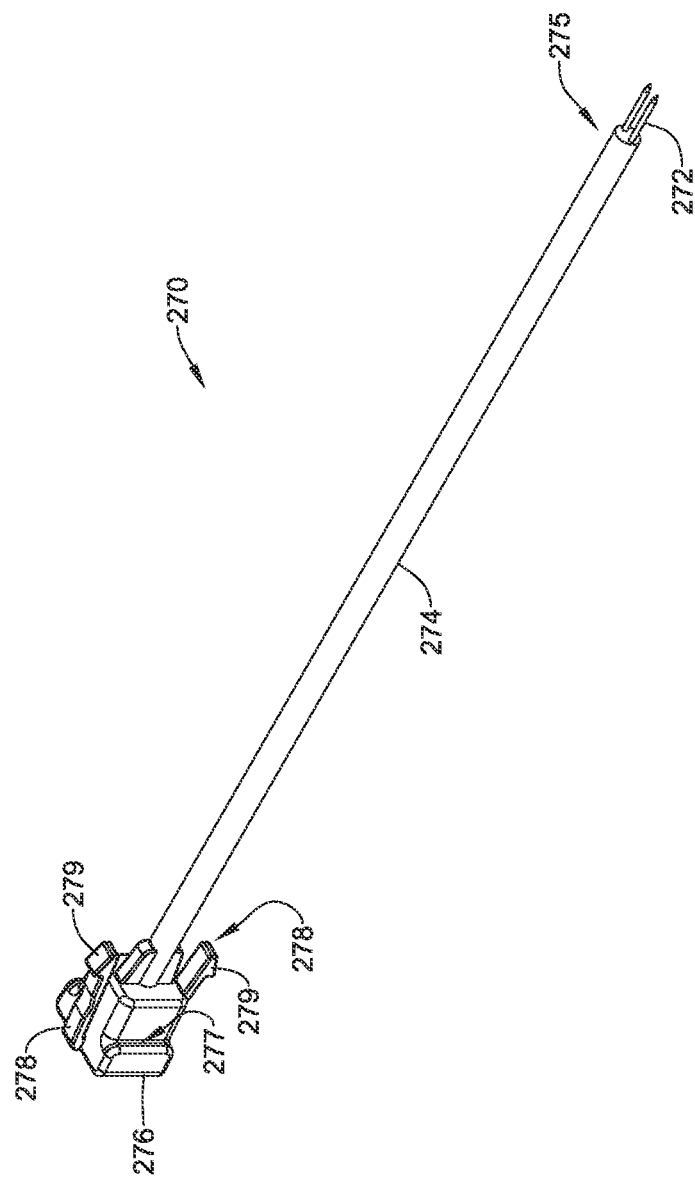
FIG. 3 is a perspective view illustrating aspects of an example bone punch.

In some embodiments, a medical device may be used to form one or more holes within a bone (e.g., the humerus 14) of a patient to facilitate placement of the one or more bone staples 100 and/or to secure the sheet-like implant 50 to the bone. In some embodiments, the medical device (e.g., FIG. 4) may include a bone punch 270 including an elongate shaft 274, a head 276 disposed at a proximal end of the elongate shaft 274, and a piercing tip 272 disposed at a distal end 275 of the elongate shaft 274, as shown in FIG. 3 for example. In some embodiments, the bone punch 270 and/or the piercing tip 272 may include a plurality of piercing tips, two or more piercing tips, a pair of piercing tips, etc. extending distally from the distal end 275 of the elongate shaft 274. The piercing tip 272 may be configured to be driven into the bone (e.g., the humerus 14). In some embodiments, the piercing tip 272 may be a spike, a prong, a spear, or other suitable shape. As such, the piercing tip 272 may include a sharpened distal end and/or a tapered distal portion configured to engage and/or penetrate bone.

In some embodiments, the head 276 of the bone punch 270 may include a plurality of connecting members 278. Each of the plurality of connecting members 278 may include an outwardly extending protrusion 279. In some embodiments, the plurality of connecting members 278 may be fixedly attached to opposing sides of the head 276. The plurality of connecting members 278 may extend from the head 276 distally toward the distal end 275 of the elongate shaft 274. The plurality of connecting members 278 may extend laterally outward from the head 276 at an oblique angle to a longitudinal axis of the bone punch 270 and/or the elongate shaft 274. In some embodiments, the plurality of connecting members 278 may be biased laterally outward from the head 276. Additional details regarding the plurality of connecting members 278 and their use will become apparent from the discussion herein.

In some embodiments, the head 276 may include one or more lateral projections. In some embodiments, the one or more lateral projections may be disposed between the plurality of connecting members 278 and/or between a proximal end of the head 276 and a distal end of the head 276. The one or more lateral projections may each and/or collectively define a distal surface 277 of the head 276. The distal surface 277 may be a distally facing surface and does not necessarily need to be a distalmost surface of the head 276. For example, the distal surface 277 may be disposed between the proximal end of the head 276 and the distal end of the head 276.

In some embodiments, the proximal end of the elongate shaft 274 may extend into the head 276 of the bone punch 270. In some embodiments, the proximal end of the elongate shaft 274 may be fixedly attached to the head 276. In some embodiments, the elongate shaft 274 may be monolithically formed with the head 276, such as by casting, molding, or machining, for example. Other configurations are also contemplated.

Similarly, a proximal end of the piercing tip 272 may extend into the distal end 275 of the elongate shaft 274. The proximal end of the piercing tip 272 may be fixedly attached to the elongate shaft 274. In some embodiments, the piercing tip 272 may be monolithically formed with the elongate shaft 274, such as by casting, molding, or machining, for example. Other configurations are also contemplated. Some examples of suitable but non-limiting materials for the bone punch 270 and/or elements or components thereof are described below.

Figure 4:
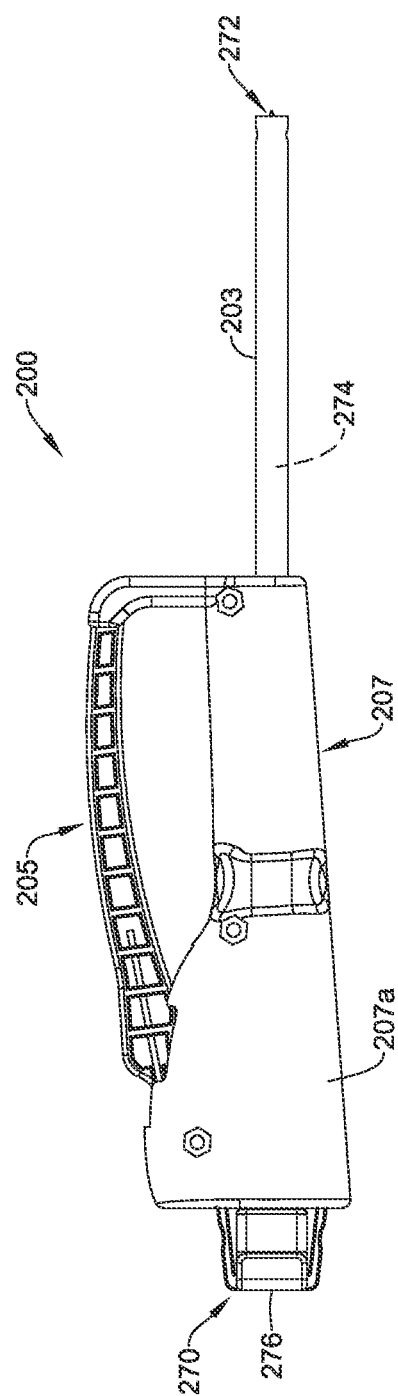
FIG. 4 is a side view illustrating aspects of an example medical device.

FIG. 4 illustrates aspects of a medical device configured to form one or more holes within a bone of a patient in a side view. The medical device may comprise a handle assembly 200 including a housing 207, a lever 205 rotatably coupled to the housing 207, and a sheath 203 extending distally from the housing 207. In at least some embodiments, a proximal end of the sheath 203 may be fixedly attached to the housing 207. The sheath 203 may extend into and/or within the housing 207, such that the proximal end of the sheath 203 is disposed within a distal portion of the housing 207, and the sheath 203 extends within the housing 207 and distally from a distal end of the housing 207. Some examples of suitable but non-limiting materials for the housing 207, the lever 205, the sheath 203, and/or elements or components thereof are described below.

The housing 207 may be formed as a multi-piece structure including a first housing portion 207A, seen in FIG. 4, and a second housing portion 207B, not visible in FIG. 4. For the purpose of illustration herein, one of the first housing portion 207A or the second housing portion 207B may be hidden from view in the figures to permit viewing of internal components and/or features thereof. The first housing portion 207A and the second housing portion 207B may be assembled together to form the housing 207. In the illustrated example(s), fasteners such as screws and nuts may be used to assemble the housing 207. However, other assembly and/or attachment means may also be used, including but not limited to snap fit, friction fit, pins, rivets, etc. In some embodiments, once the housing 207 is assembled, such assembly may be considered and/or made permanent using any known suitable means, such as but not limited to adhesives, welding, etc.

Figure 5:
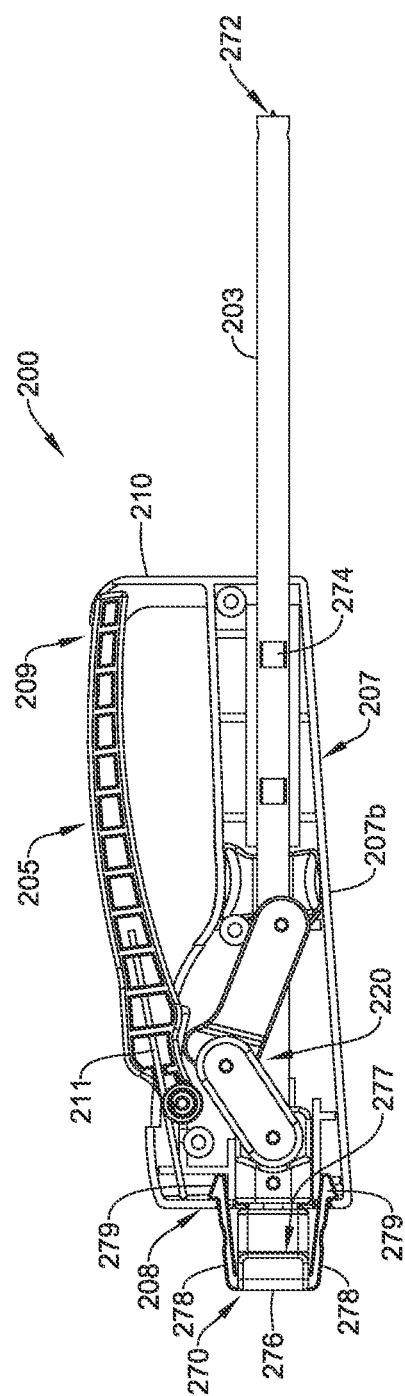
FIG. 5 illustrates aspects of the medical device of FIG. 4 with the lever in an initial or intermediate position.

The medical device may include the bone punch 270 described herein. The bone punch 270 may be disposed within and/or extend through the sheath 203. The head 276 of the bone punch 270 may be releasably engaged with the housing 207 in a first position, as shown in FIGS. 4-5. The piercing tip 272 may be positioned proximate a distal end of the sheath 203 in the first position. In some embodiments, the piercing tip 272 may be disposed within the distal end of the sheath 203 in the first position. In some embodiments, a portion of the piercing tip 272 may extend distally of the distal end of the sheath 203 in the first position to aid in positioning the medical device at a treatment site (e.g., to engage a surface of the bone). In some embodiments, less than 50% of the piercing tip 272 extends distally of the distal end of the sheath 203 in the first position. In some embodiments, less than 40% of the piercing tip 272 extends distally of the distal end of the sheath 203 in the first position. In some embodiments, less than 30% of the piercing tip 272 extends distally of the distal end of the sheath 203 in the first position. In some embodiments, less than 20% of the piercing tip 272 extends distally of the distal end of the sheath 203 in the first position. In some embodiments, less than 10% of the piercing tip 272 extends distally of the distal end of the sheath 203 in the first position. In some embodiments, less than 5% of the piercing tip 272 extends distally of the distal end of the sheath 203 in the first position.

FIG. 5 illustrates the medical device with the first housing portion 207A of the handle assembly 200 removed and the second housing portion 207B visible. The housing 207 may include a leg 210 extending laterally from a distal portion thereof. In some embodiments, the leg 210 may be disposed at and/or extend laterally from the distal end of the housing 207. The lever 205 may be rotatably and/or pivotably coupled to the housing 207 about an axis of rotation. The handle assembly 200 may include a spring 211 biasing the lever 205 toward an initial position, such as an intermediate position. In at least some embodiments, the spring 211 may include a coiled portion disposed about and/or coaxial with the axis of rotation of the lever 205.

In FIG. 5, the lever 205 is shown disposed in the initial or intermediate position. In at least some embodiments, from the initial or intermediate position, the lever 205 may be configured to rotate a distal end 209 of the lever 205 toward or away from the housing 207. In the initial or intermediate position, the distal end 209 of the lever 205 may be substantially aligned with and/or disposed within a free end of the leg 210. In the initial or intermediate position, the lever 205 may extend distally toward a distal end of the sheath 203 and/or the handle assembly 200 at a first angle relative to a longitudinal axis of the sheath 203. For example, the first angle may be less than about 15 degrees, less than about 10 degrees, less than about 5 degrees, about 0 degrees, or another small, oblique angle. In some embodiments, in the initial or intermediate position, the lever 205 may extend toward the distal end of the sheath 203 generally parallel to a longitudinal axis of the sheath 203.

In FIG. 5, the bone punch 270 is shown disposed in the first position. The elongate shaft 274 of the bone punch 270 is slidably disposed within the sheath 203 of the handle assembly 200 when the lever 205 is in the initial or intermediate position. The head 276 of the bone punch 270 may be releasably engaged with the housing 207 of the handle assembly 200 in the first position and/or when the lever 205 is in the initial or intermediate position. For example, the plurality of connecting members 278 and the outwardly extending protrusion(s) 279 thereof may engage a wall of the housing 207 defining a proximal surface 208 of the housing 207. In some embodiments, the proximal surface 208 may be a proximally facing surface of the housing 207 at and/or proximate a proximal end of the housing 207. In some embodiments, the proximal surface 208 may be a proximalmost surface of the housing 207.

In the first position, the outwardly extending protrusion(s) 279 may extend laterally outward from the head 276 and/or the longitudinal axis of the bone punch 270 and/or the elongate shaft 274 beyond a perimeter of an opening in the wall of the housing 207 within which the head 276 is disposed. The outwardly extending protrusion(s) 279 may prevent the head 276 and/or the bone punch 270 from being removed from the housing 207 until the plurality of connecting members 278 are squeezed, urged, actuated, or otherwise moved inward toward the head 276, and/or the longitudinal axis of the bone punch 270 and/or the elongate shaft 274, to disengage the outwardly extending protrusion(s) 279 from the wall of the housing 207 by translating the outwardly extending protrusion(s) 279 inward until the outwardly extending protrusion(s) 279 are disposed within and/or inward of the perimeter of the opening. Doing so will permit the plurality of connecting members 278 and the outwardly extending protrusion(s) 279 to pass through the opening in the wall of the housing 207. In the first position, the one or more lateral projections of the head 276 and/or the distal surface 277 of the head 276 may be spaced apart proximally from the proximal surface 208 of the wall of the housing 207.

Figure 6:
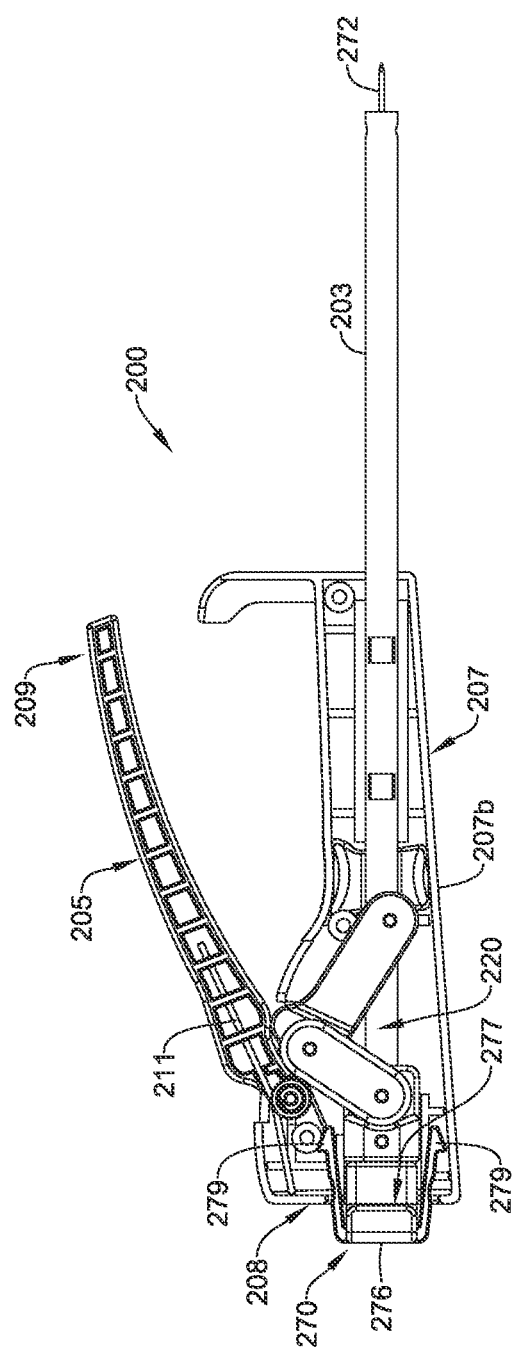
FIG. 6 illustrates aspects of the medical device of FIG. 4 with the lever in an extended position.

In some embodiments, the handle assembly 200 may include a linkage 220 disposed within the housing 207. The linkage 220 will be described in more detail with respect to FIGS. 7-10. As may be seen in FIG. 5, the head 276 of the bone punch 270 may engage the linkage 220 in the first position. The linkage 220 may be pivotably engaged with and/or coupled to the housing 207. The linkage 220 may include a plurality of elements that are movable and/or pivotable relative to each other. Translation of the bone punch 270 distally within the sheath 203, and/or translation of the head 276 of the bone punch 270 distally relative to the housing 207, from the first position to a second position distal of the first position may cause the linkage 220 to rotate the distal end 209 of the lever 205 away from the housing 207 and/or away from the longitudinal axis of the bone punch 270 and/or the elongate shaft 274 to an extended position, as shown in FIG. 6. In the extended position, the lever 205 may extend toward a distal end of the sheath 203 and/or the handle assembly 200 at a second angle relative to the longitudinal axis of the sheath 203. In some embodiments, the second angle may be an oblique angle. The second angle may be greater than the first angle.

As shown in FIG. 6, the distal surface 277 of the head 276 of the bone punch 270 may engage and/or abut the proximal surface 208 of the housing 207 in the second position. In the second position, the outwardly extending protrusion(s) 279 may be spaced apart distally from the wall of the housing 207 defining the proximal surface 208. However, the outwardly extending protrusion(s) 279 may still extend laterally outward from the head 276 and/or the longitudinal axis of the bone punch 270 and/or the elongate shaft 274 beyond the perimeter of the opening in the wall of the housing 207 within which the head 276 is disposed, thus preventing inadvertent removal of the bone punch 270 from the handle assembly 200.

In the second position, the piercing tip 272 may be extended from the distal end of to the sheath 203 as the elongate shaft 274 is translated distally within the sheath 203. The distal end of the sheath 203 may be configured to be disposed adjacent a surface of the bone. As the bone punch 270 is translated distally to the second position, the piercing tip 272 may be driven into the bone to form one or more holes in the bone. There may be a direct or indirect correlation between a rotational position of the lever 205 relative to the housing 207 and a depth of the piercing tip 272 within the bone. As the lever 205 rotates farther away from the housing 207 and/or as an angle between the lever 205 and the longitudinal axis of the sheath 203 and/or the bone punch 270 increases, the piercing tip 272 may be extended farther distally from the distal end of the sheath 203 and/or may be driven farther into the bone. A user of the medical device and/or the handle assembly 200 may be able to use the rotational position of the lever 205 relative to the housing 207 and/or the longitudinal axis of the sheath 203 and/or the bone punch 270 to indicate the depth of the piercing tip 272 within the bone, thereby providing a visual cue to the user about the status of the procedure.

Thereafter, rotation of the lever 205 from the extended position (e.g., FIG. 6) toward the initial or intermediate position (e.g., FIG. 5) may generate proximal force on the bone punch 270 sufficient to overcome cortical elasticity of the bone (which is "squeezing" or "pinching" the piercing tip 272) to extract the piercing tip 272 from the bone. Accordingly, rotation of the lever 205 from the extended position (e.g., FIG. 6) toward the initial or intermediate position (e.g., FIG. 5) may generate proximal translation of the bone punch 270 to thereby extract the piercing tip 272 from the bone, leaving the one or more holes formed in the bone. The linkage 220 may provide a mechanical advantage in generating the force necessary to extract the piercing tip 272 from the bone, thereby reducing the force that the user needs to exert on the lever 205. Rotating the lever 205 from the extended position to the initial or intermediate position may translate the bone punch 270 from the second position back to the first position. Thereafter, the bone punch 270 may be removed from the handle assembly 200 if desired, or the medical device may be removed from the treatment site.

Figure 7:
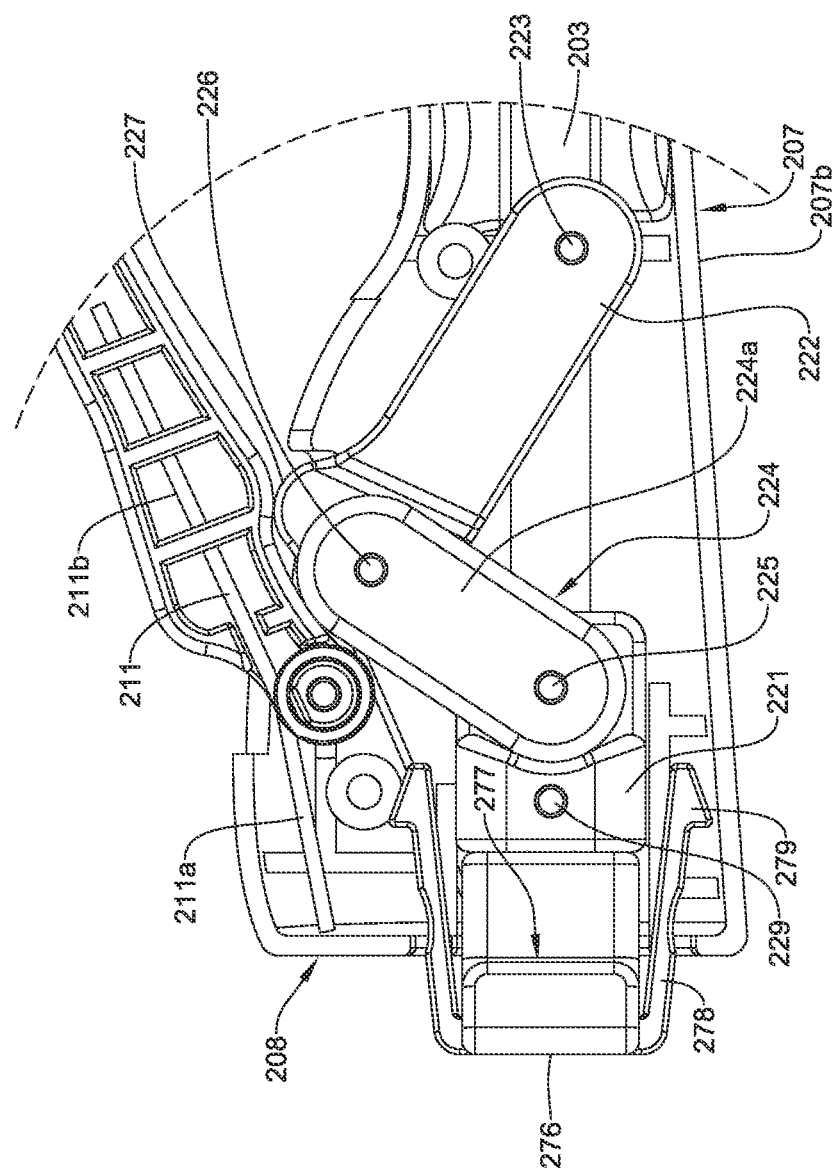
FIG. 7 is a detailed view illustrating aspects of the medical device of FIG. 4 with the lever in the extended position of FIG. 6.

FIG. 7 is a detailed view of a portion of the medical device of FIG. 6, wherein the bone punch 270 is disposed in the second position and the lever 205 is disposed in the extended position. The linkage 220 may include an ejector block 221 slidably disposed within the housing 207. The ejector block 221 may include one or more pins 229 configured to engage the housing 207 and/or configured to slide longitudinally and/or axially within a channel formed in the housing 207. In some embodiments, the ejector block 221 may be configured to slide longitudinally and/or axially within a channel formed in the housing 207. In some embodiments, the ejector block 221 may be configured to slide parallel to the longitudinal axis of the sheath 203 and/or the longitudinal axis of the bone punch 270 and/or the elongate shaft 274. In some embodiments, the sheath 203 may extend through and/or may pass through the ejector block 221. As such, the ejector block 221 may be slidably disposed about the sheath 203. Since the elongate shaft 274 may be slidably disposed within the sheath 203, the elongate shaft 274 may also extend through the ejector block 221. The head 276 of the bone punch 270 may be configured to engage the ejector block 221 in the first position. During distal translation of the bone punch 270 from the first position to the second position, the head 276 of the bone punch 270 may push, urge, or otherwise translate the ejector block 221 distally within the housing 207, thereby actuating the linkage 220 and causing the linkage 220 to rotate the distal end 209 of the lever 205 away from the housing 207 to the extended position.

In at least some embodiments, the linkage 220 may further include a distal link 222 pivotably engaged with the housing 207 at a distal pivot point 223, and a middle link 224 pivotably engaged with the ejector block 221 at a proximal pivot point 225. In some embodiments, the middle link 224 may include a first middle link 224A and a second middle link 224B (not shown). In some embodiments, a proximal portion of the distal link 222 may be disposed between the first middle link 224A and the second middle link 224B. In some embodiments, a distal portion of the distal link 222 may comprise a pair of opposing legs extending on opposite sides of the sheath 203. One leg of the pair of opposing legs may be configured to engage the first housing portion 207A, and one leg (e.g., the opposite leg) of the pair of opposing legs may be configured to engage the second housing portion 207B.

The distal link 222 may be pivotably engaged with the middle link 224 at an intermediate pivot point 226 between the distal pivot point 223 and the proximal pivot point 225. The distal pivot point 223 may be axially and/or longitudinally fixed relative to the housing 207. As such, when the head 276 of the bone punch 270 is translated distally to slide the ejector block 221 distally within the housing 207, a proximal end of the distal link 222 and a distal end of the middle link 224 may be translated laterally relative to the longitudinal axis of the sheath 203, the bone punch 270, and/or the elongate shaft 274 by pivoting relative to each other at the intermediate pivot point 226 as a proximal end of the middle link 224 is translated distally and/or longitudinally toward a distal end of the distal link 222 and/or the distal pivot point 223. In some embodiments, the proximal pivot point 225, the intermediate pivot point 226, and/or the distal pivot point 223 may include and/or be defined by one or more pins, shafts, or other elements. Some examples of suitable but non-limiting materials for the ejector block 221, the distal link 222, the middle link 224, and/or elements or components thereof are described below. The distal link 222 may include a cam surface 227 configured to engage a corresponding surface of the lever 205, wherein the corresponding surface of the lever 205 faces toward the housing 207, the distal link 222, and/or the longitudinal axis of the sheath 203, the bone punch 270, and/or the elongate shaft 274. In some embodiments, the cam surface 227 may be a curved surface. In some embodiments, the cam surface 227 may be a convex surface. In some embodiments, the corresponding surface of the lever 205 may be a curved surface. In some embodiments, the corresponding surface of the lever 205 may be a convex surface. In some embodiments, the corresponding surface of the lever 205 may be a concave surface. In some embodiments, the corresponding surface of the lever 205 may be a complex and/or an irregular surface having both concave and convex portions. Other configurations are also contemplated.

As discussed above, the handle assembly 200 may include a spring 211 disposed within the housing 207. The spring 211 may include a first arm portion 211A extending proximally from the coiled portion and configured to engage the housing 207. In at least some embodiments, the first arm portion 211A may be configured to engage the first housing portion 207A (not shown). The spring 211 may include a second arm portion 211B extending distally from the coiled portion and configured to engage the lever 205. For example, the lever 205 may include a slot formed therein configured to receive the second arm portion 211B. In another example, the lever 205 may include one or more apertures 206 configured to receive the second arm portion 211B, as seen in FIG. 8.

Figure 8:
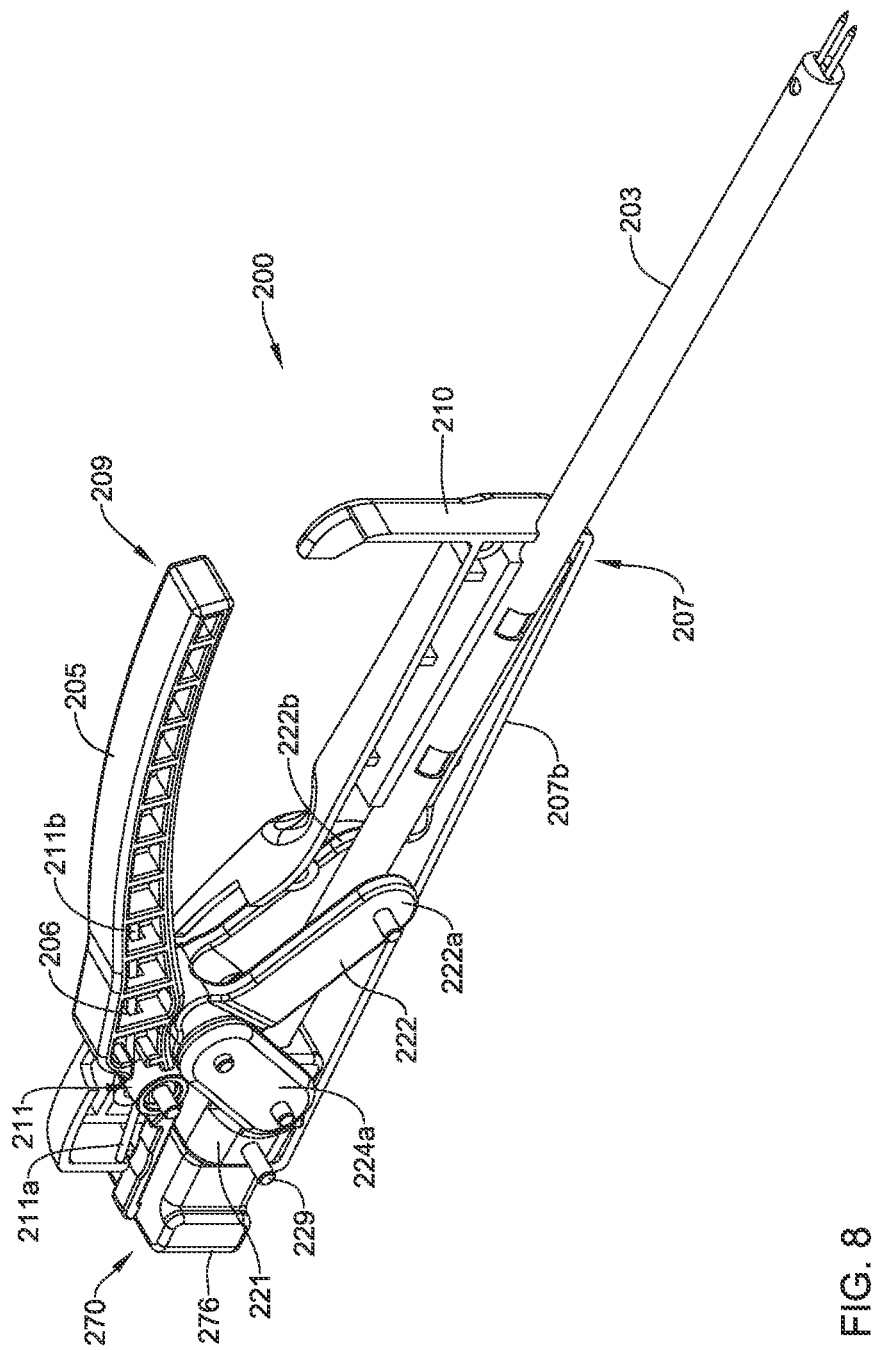
FIGS. 8-10 are perspective views illustrating aspects of the medical device of FIG. 4 with the lever in the extended position of FIG. 6.
Figure 9:
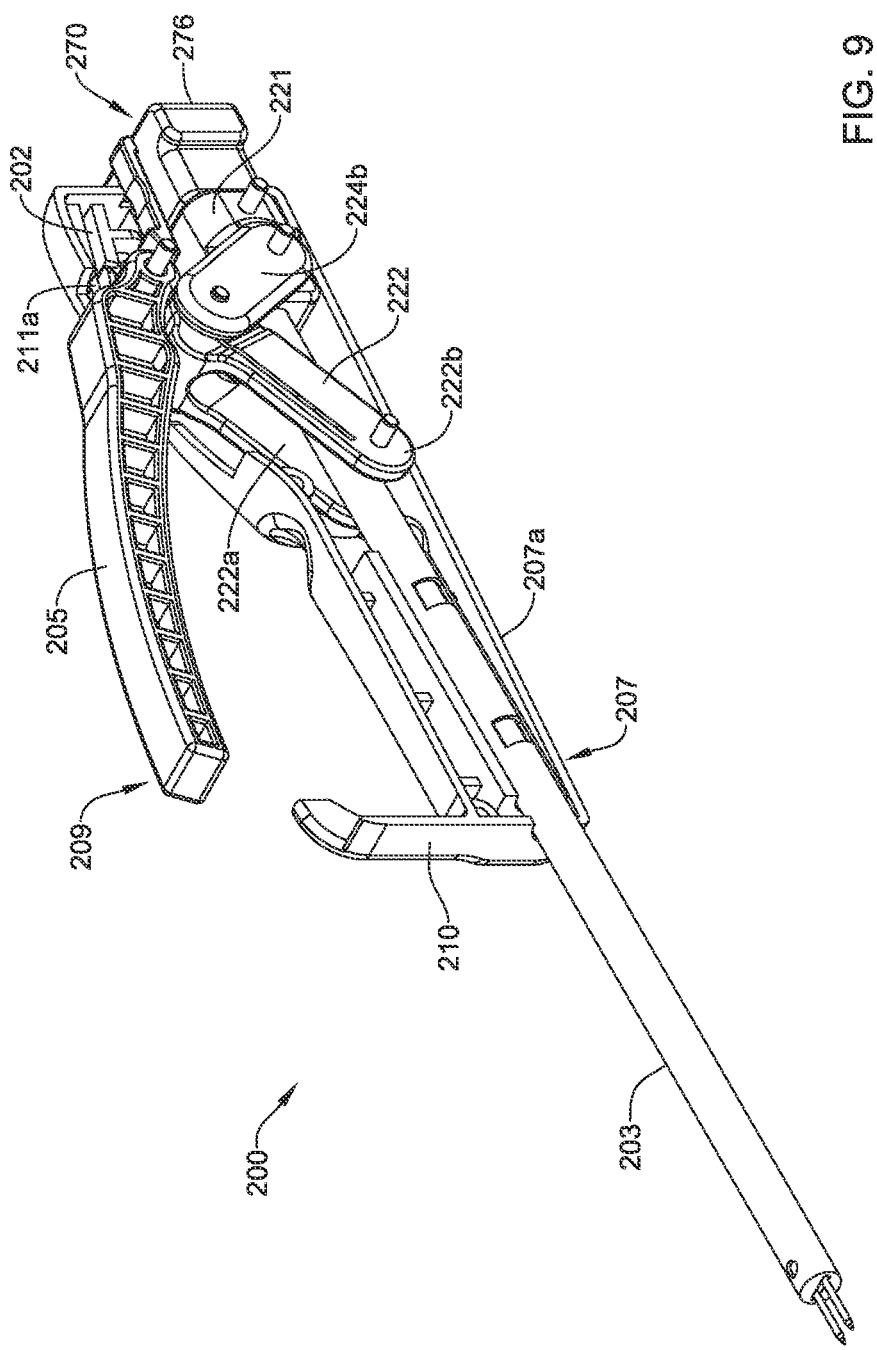
Figure 10:
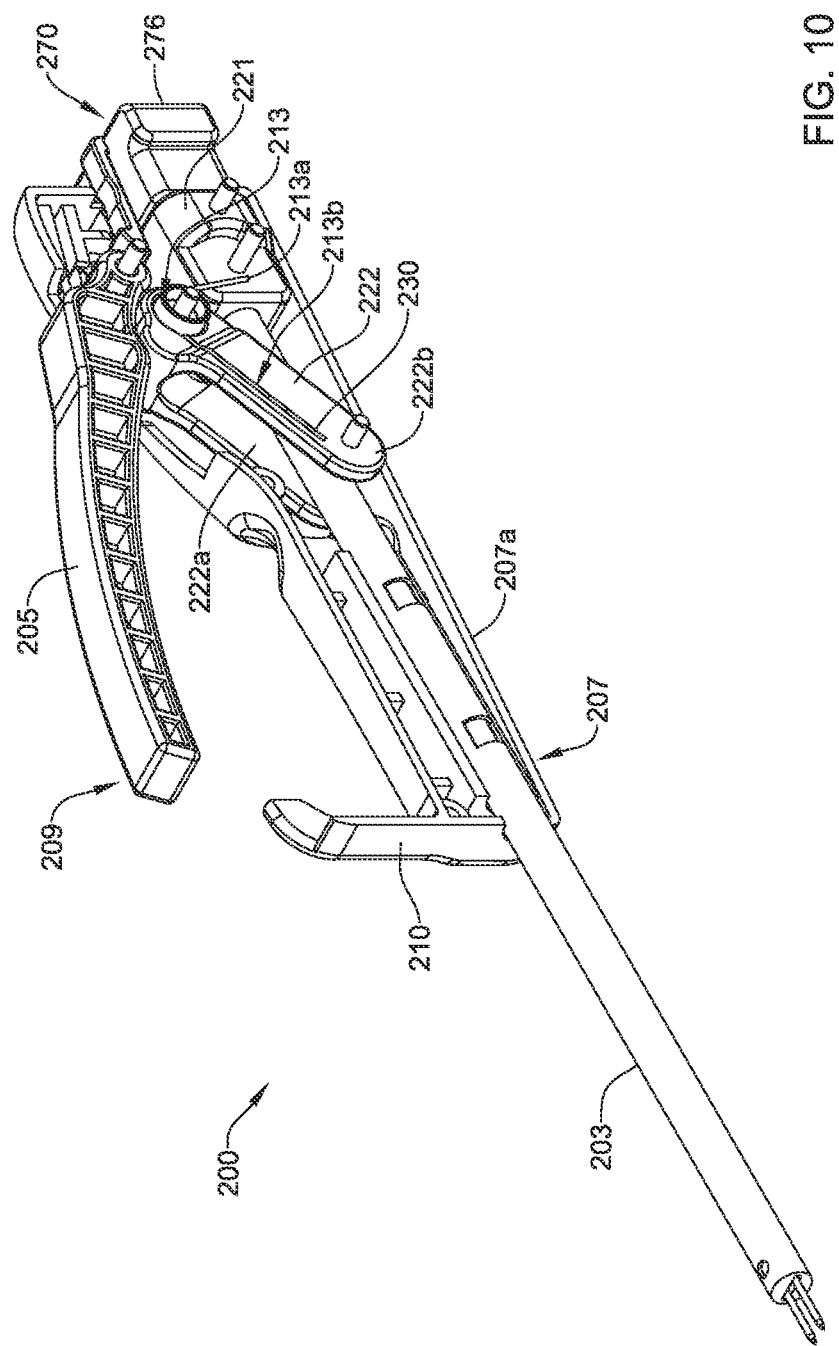

FIGS. 8-10 are perspective views of the medical device and the handle assembly 200 described herein. FIGS. 8-10 are shown from different angles and with different elements of the handle assembly 200 hidden from view show additional features and/or to facilitate understanding of the various interactions between components. For example, in some embodiments, the pair of opposing legs of the distal link 222 may include a first leg 222A and a second leg 222B. In some embodiments, the first housing portion 207A may include a slot 202 configured to receive the first arm portion 211A of the spring 211, as seen in FIG. 9. Other configurations for securing the first arm portion 211A relative to the first housing portion 207A, and/or preventing relative movement therebetween, are also contemplated. As discussed above, the middle link 224 may include a first middle link 224A (not shown) and a second middle link 224B, shown in FIG. 9. The first middle link 224A and the second middle link 224B may be similar in form, size, and/or shape.

In some embodiments, the handle assembly 200 may include a second spring 213, shown in FIG. 10, may include a coiled portion, a first arm portion 213A extending proximally from the coiled portion, and a second arm portion 213B extending distally from the coiled portion. In some embodiments, the second middle link 224B (not shown) may include a slot formed therein facing and/or opening inwardly and/or toward the proximal portion of the distal link 222. The slot formed in the second middle link 224B may be configured to receive the first arm portion 213A of the second spring 213. The distal link 222 may include a slot 230 formed in the second leg 222B of the pair of opposing legs of the distal link 222, wherein the slot 230 faces and/or opens outwardly and/or toward the second middle link 224B. The slot 230 may be configured to receive the second arm portion 213B of the second spring 213. In some embodiments, at least a portion of the coiled portion of the second spring 213 may be received and/or recessed in the proximal portion of the distal link 222.

Figure 11:
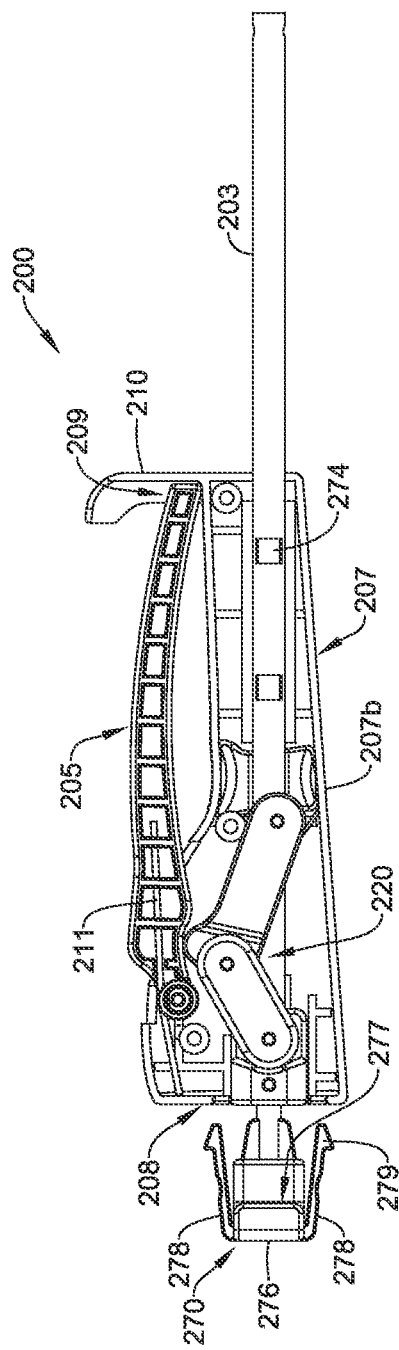
FIG. 11 illustrates aspects of the medical device of FIG. 4 with the lever in a disengagement position.

It will be easily understood that rotation of the lever 205 toward the housing 207 and/or the longitudinal axis of the sheath 203, the bone punch 270, and/or the elongate shaft 274 (e.g., toward the initial or intermediate position) when the bone punch 270 is in the second position may actuate the linkage 220 to translate the head 276 of the bone punch 270 proximally to retract the piercing tip 272 into the sheath 203 and/or to extract the piercing tip 272 from the bone of the patient. The corresponding surface of the lever 205 may exert a force upon the cam surface 227 of the distal link 222, thereby urging and/or translating the proximal portion of the distal link 222 laterally toward the longitudinal axis of the sheath 203, the bone punch 270, and/or the elongate shaft 274, thereby resulting in corresponding movement of the middle link 224 and proximal translation of the ejector block 221 within the housing 207 until the outwardly extending protrusion(s) 279 re-engage the wall of the housing 207. When the outwardly extending protrusion(s) 279 are engaged with the wall of the housing 207, the lever 205 is in the initial or intermediate position and is prevented from rotating inward past the initial or intermediate position and/or closer to the housing 207 than the initial or intermediate position until the outwardly extending protrusion(s) 279 are disengaged from the wall of the housing 207 by squeezing, urging, actuating, or otherwise moving the plurality of connecting members 278 inward toward the head 276, and/or the longitudinal axis of the bone punch 270 and/or the elongate shaft 274. Once the outwardly extending protrusion(s) 279 are disengaged from the wall of the housing 207, the lever 205 may be rotated toward the housing 207 and/or the longitudinal axis of the sheath 203, the bone punch 270, and/or the elongate shaft 274 toward a disengagement position, shown in FIG. 11, to aid in ejecting the bone punch 270 from the handle assembly 200.

The spring 211 may be biased toward the initial or intermediate position of the lever 205. As such, if the lever 205 is rotated away from the initial or intermediate position, the spring 211 may be stressed and may exert a force on the lever 205 to return the lever 205 to the initial or intermediate position. The initial or intermediate position of the lever 205 may be considered a "home" position for the spring 211. Similarly, the second spring 213 may be biased toward the disengagement position of the lever 205. As such, if the lever 205 is rotated away from the disengagement position, the second spring 213 may be stressed and may exert a force on the linkage 220 to return the lever 205 to the disengagement position. The disengagement position of the lever 205, and the corresponding positioning of the linkage 220, may be considered a "home" position for the second spring 213. The spring 211 may be configured to exert a greater force on the lever 205 than the second spring 213 is configured to exert on the linkage 220. Effectively, the spring 211 is "stronger" than the second spring 213 and the force exerted by the spring 211 may override the force exerted by the second spring 213. This relationship may also require less force to be applied to the lever 205 to rotate the lever 205 from the extended position toward the initial or intermediate position and/or the disengagement position than to rotate the lever 205 from the initial or intermediate position to the extended position. In other instances, the handle assembly 200 may be configured such that the second spring 213 may be configured to exert a greater force on the lever than the spring 211. If all external forces are removed from the handle assembly 200, the lever 205 will be biased toward and/or will return to the initial or intermediate position. If the bone punch 270 is not present within the handle assembly 200, the lever 205 will be biased toward and/or will return to the initial or intermediate position.

Figure 12:
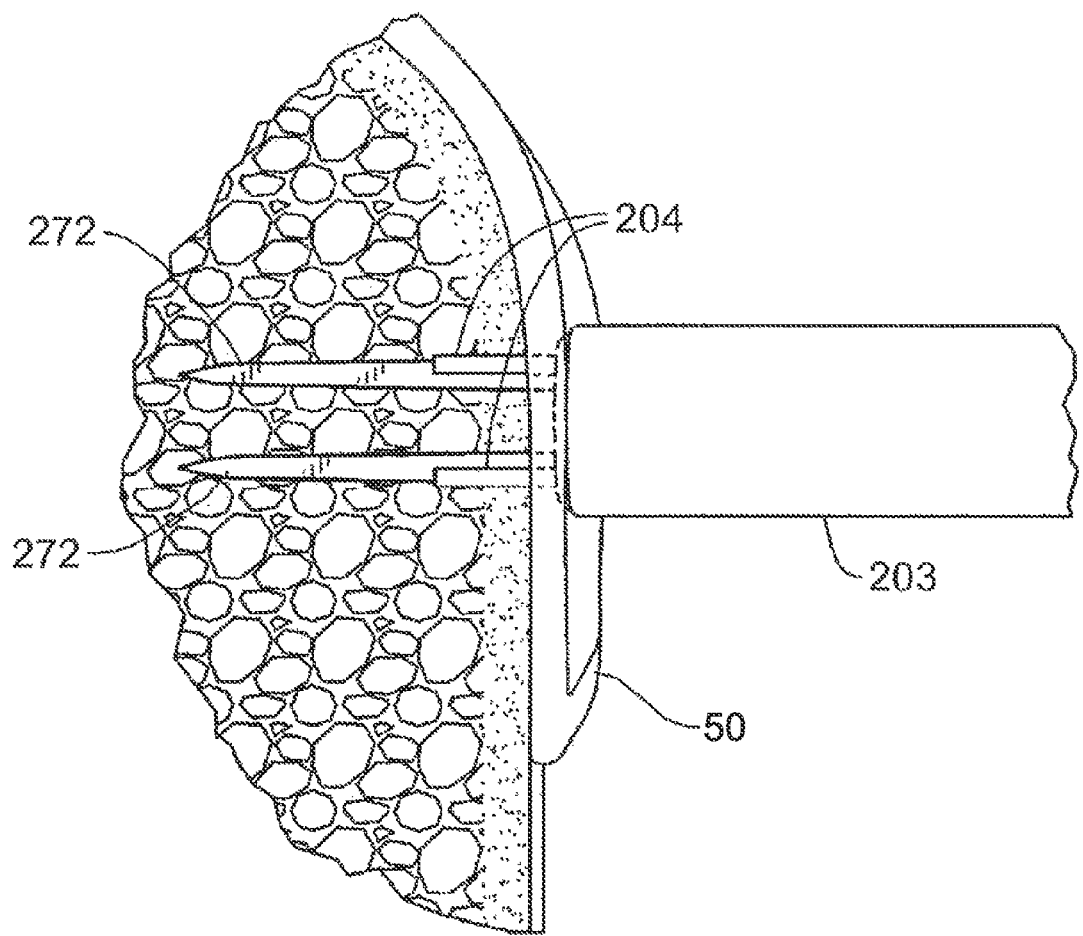
FIG. 12 is a partial cross-sectional view depicting the medical device of FIG. 4 and the bone punch of FIG. 3 disposed at an implant site after the bone punch has been driven into bone at the implant site.

In use, the distal end of the sheath 203 may be configured to be positioned adjacent and/or against the surface of a bone of the patient. As discussed herein, the medical device may be configured to form one or more holes within the bone. In some embodiments, the distal end of the sheath 203 may be positioned directly against the surface of the bone. In some embodiments, the distal end of the sheath 203 may be positioned against a sheet-like implant 50 that is positioned directly against the surface of the bone, as shown in FIG. 12 for example, so that the one or more holes may also be formed in the sheet-like implant 50. As such, the presence of the sheet-like implant 50 as positioned in FIG. 12 may be considered optional.

Figure 13:
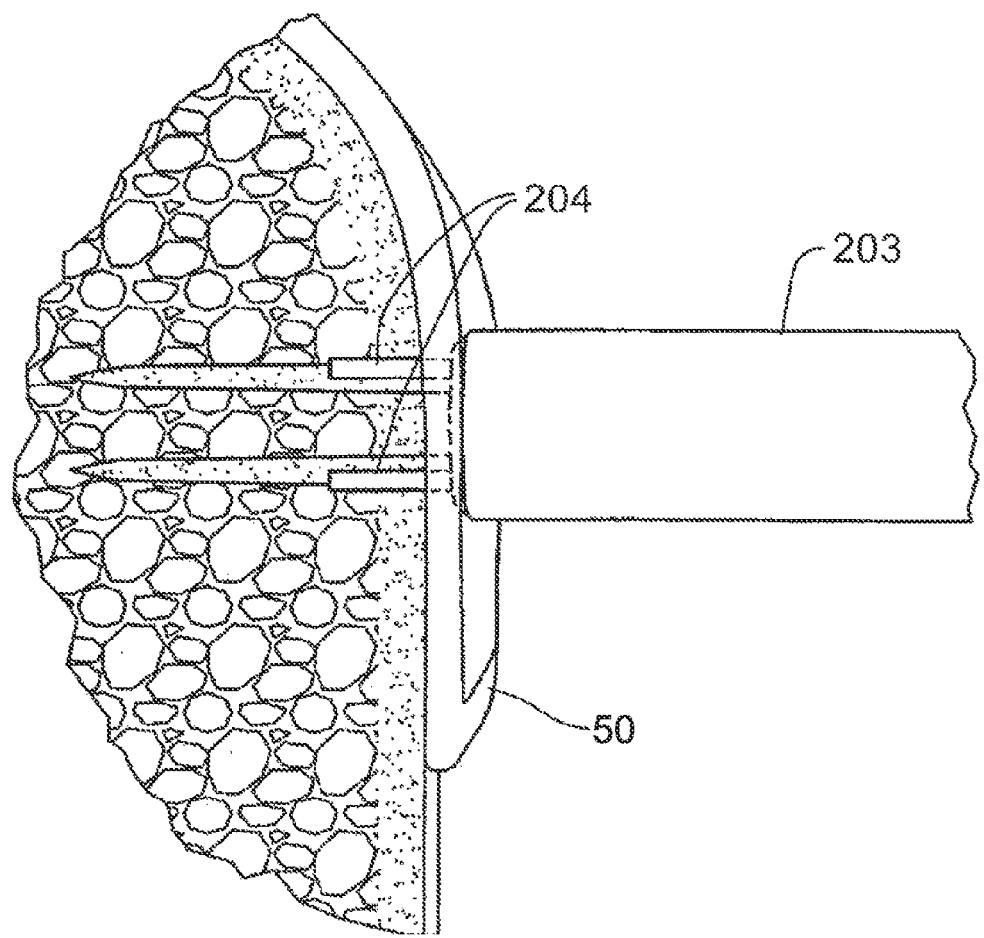
FIG. 13 is a partial cross-sectional view depicting the medical device of FIG. 4 and the bone punch of FIG. 3 disposed at an implant site after the bone punch has been driven into and removed from bone at the implant site.

After positioning the piercing tip 272 against the surface of the bone, the user may apply distal force to the head 276 of the bone punch 270, such as with a mallet or other tool, to drive the piercing tip 272 into the bone, as seen in FIG. 12. In some embodiments, the sheath 203 may optionally include position retention members 204 extending distally therefrom, wherein the position retention members 204 are configured to extend into the one or more holes formed in the bone as the piercing tip 272 is driven distally into the bone. Next, as the lever 205 is rotated toward the housing 207 to extract the piercing tip 272 from the bone, the position retention members 204 may remain positioned within the one or more holes to maintain the position of the sheath 203 and/or the handle assembly 200 relative to the one or more holes, as seen in FIG. 13.

Figure 14:
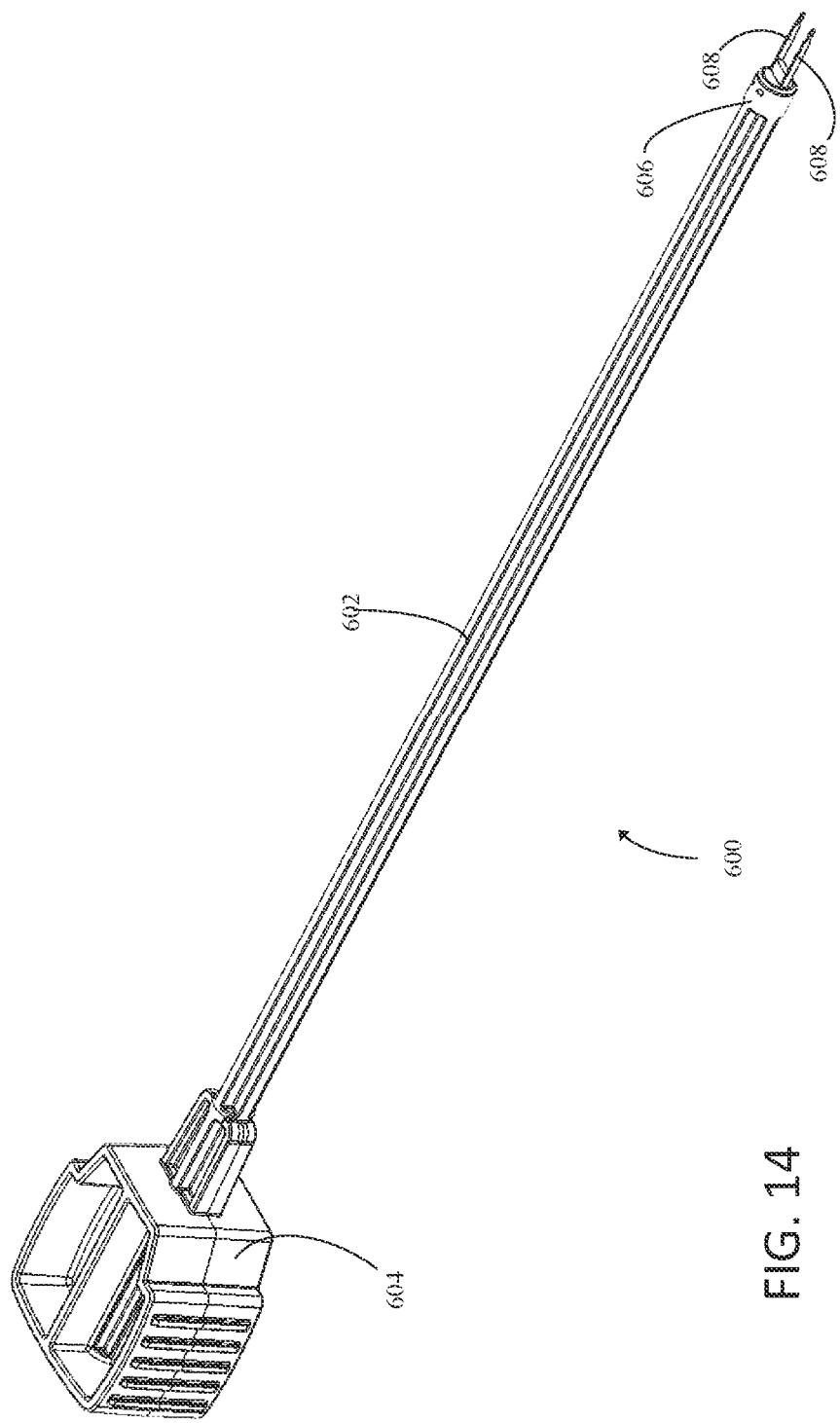
FIG. 14 is a perspective view of an example bone staple inserter.

In some embodiments, after disengaging the bone punch 270 from the housing 207 and/or after removing the bone punch 270 from the handle assembly 200, the user may insert a staple delivery insert 600, as depicted in FIG. 14, into the sheath 203 of the handle assembly 200. The staple delivery insert 600 may be comprised of a shaft 602, a proximal head 604, and a distal end 606. The staple delivery insert 600 may have arms 608 connected to the distal end 606 which may retain a bone staple, such as a bone staple 100, shown and described in more detail with respect to FIG. 15. In some examples, the arms 608 may be designed to be received into the cavities 128A, 128B of the bone staple 100 and retain the bone staple 100 with friction. Once the staple delivery insert 600 is received within the sheath 203, the user may then apply force to the proximal end of the staple delivery insert 600. The applied force may drive the arms 610 of the staple delivery insert 600, along with the bone staple 100, into the one or more holes formed in the bone. Natural movement of tissue and/or the bone, and/or a pullout force applied to the bridge of the bone staple 100, may act to secure the bone staple 100 within the bone.

The user may then remove the staple delivery insert 600 from handle assembly 200. The bone may impart a holding force on the bone staple 100 sufficient to overcome the friction force between the arms 608 of the staple delivery insert 600 and the bone staple 100 such that the staple delivery insert 600 may be removed from the bone while the bone staple 100 remains in the bone. Finally, the user may then retract the handle assembly 200 from the patient and finish the procedure.

Figure 15:
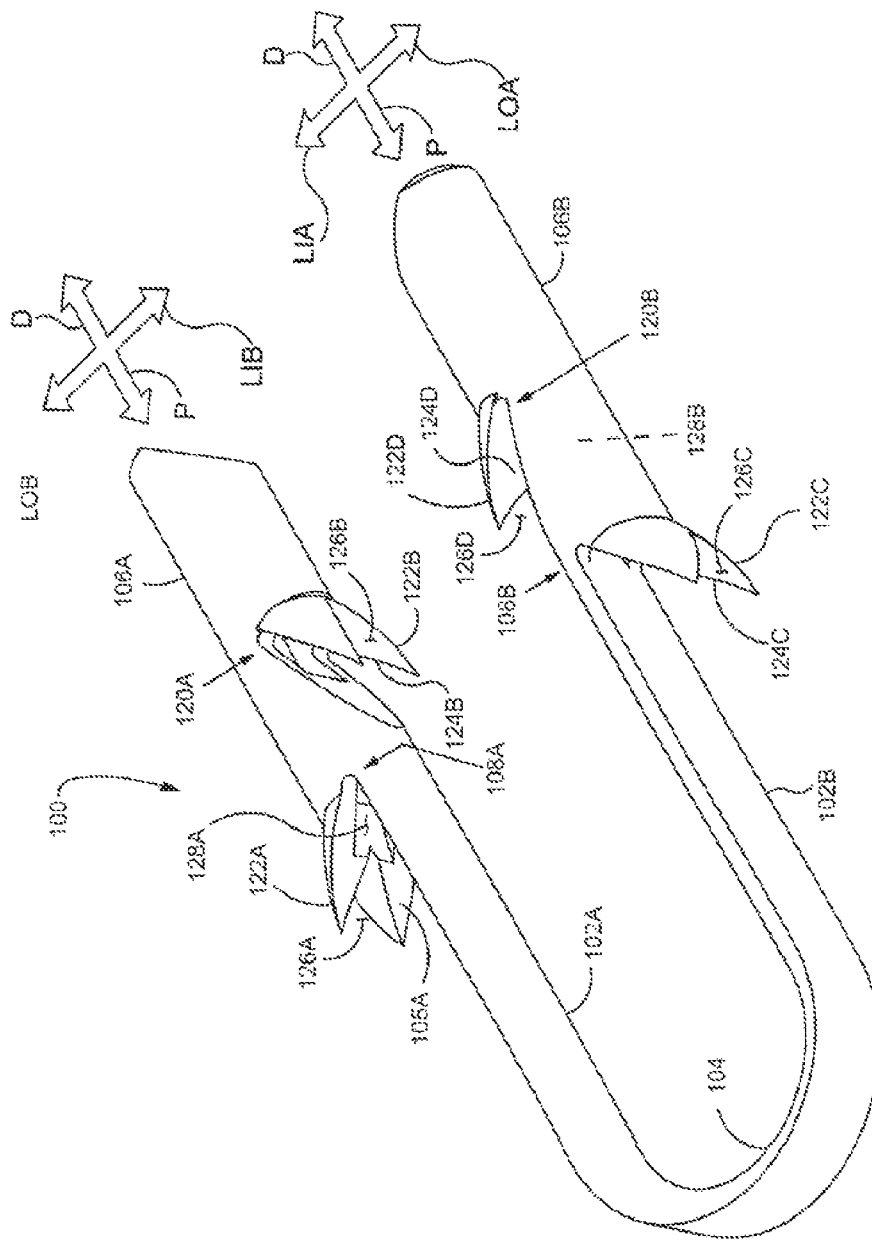
FIG. 15 is a perspective view of an example bone staple.

FIG. 15 illustrates an example bone staple 100 that may be used with the medical device(s) described herein. Although the various parts of the exemplary bone staple 100 are depicted in relative proportion to other parts of the bone staple 100, other configurations in size and orientation of the various parts are also contemplated in other examples. A number of reference directions are illustrated using arrows in FIG. 15 to assist in understanding the details of the bone staple 100. The illustrated directions include: proximal direction P, distal direction D, first laterally outward direction LOA, second laterally outward direction LOB, first laterally inward direction LIA, and second laterally inward direction LIB.

In some examples, the bone staple 100 comprises a first arm 102A, a second arm 102B, and a bridge 104. The bridge 104 may abut, or extend from or adjacent to, a proximal end of the first arm 102A to a proximal end of the second arm 102B. First arm 102A may include a first trunk 106A, with the first trunk 106A generally having a greater width than the rest of the first arm 102A as depicted in FIG. 15. In some examples, the first arm 102A may also include a non-trunk portion 105A. The length of the first trunk 106A relative to the overall length of the first arm 102A can vary in different examples. For instance, the first trunk 106A can extend for the entire length of the first arm 102A such that the bridge 104 abuts with or is adjacent to the first trunk 106A. In other examples, the first arm 102A may not include the first trunk 106A. That is, the first arm 102A may not have a portion with a greater width than the rest of the first arm 102A. In such examples, the first arm 102A may still have the non-trunk portion 105A.

Similarly, the second arm 102B may include a second trunk 106B, with the second trunk 106B generally having a greater width than the rest of the second arm 102B. Additionally, the second trunk 106B may extend for at least a portion of the second arm 102B. A distal portion of the second arm 102B may abut a proximal end of the second trunk 106B and in some embodiments, the second arm 102B may further include a non-trunk portion similar to the non-trunk portion 105A. As with the first trunk 106A, the second trunk 106B may extend along the second arm 102B for varying lengths. Additionally, in some examples, the second arm 102B may not have a portion with a greater width than the rest of the second arm 102B. In FIG. 15, the first trunk 106A and the second trunk 106B are shown extending distally from a proximal portion of the first arm 102A and the second arm 102B, respectively.

In the example of FIG. 15, the first trunk 106A has a lateral extent, or cross-sectional area, that is larger than a lateral extent of the non-trunk portion 105A of the first arm 102A and the bridge 104. The bone staple 100 may include a first change in lateral stiffness 108A disposed where the distal end of the non-trunk portion 105A of the first arm 102A abuts the first trunk 106A. As depicted, the change in stiffness is abrupt, but can be gradual in alternative examples—such as through a gradual change in lateral extent between the first trunk 106A and the non-trunk portion 105A. In an example where the first trunk 106A extends for the full length of the first arm 102A, the change in stiffness may occur where the first trunk 106A abuts the bridge 104. With reference to the example of FIG. 15, it will be appreciated that the first trunk 106A is mounted eccentrically to the first arm 102A and the second trunk 106B is mounted eccentrically to the second arm 102B. As with the first trunk 106A, the second trunk 106B has a lateral extent, or cross-sectional area that is larger than a lateral extent of the non-trunk portion 105B of the second arm 102B and the bridge 104. The bone staple 100 may include a second change in lateral stiffness 108B where the distal end of the non-trunk portion 105B of the second arm 102B abuts the second trunk 106B. Similarly to the first arm 102A, in some examples, the change in stiffness may be abrupt or gradual. If the second trunk 106B extends for the entire length of the second arm 102B, the change in stiffness may occur at the abutment with the bridge 104. In additional examples where there may be no change in lateral extent between the first and second trunks 106A, 106B and the first and second arms 102A, 102B, respectively, a change in stiffness may be accomplished by the use of different materials for the first and second trunks 106A, 106B and the first and second arms 102A, 102B.

Some examples of the bone staple 100 may include at least a first projection 122A and a second projection 122B on the first trunk 106A, and a third projection 122C and a fourth projection 122D on the second trunk 106B. The first and third projections 122A, 122C on the first and second trunks 106A, 106B, respectively, may further include a first proximal surface 124A and a third proximal surface 124C, respectively, each extending away from its respective trunk in a first direction, such as out and away from each opposite trunk 106A, 106B. The first direction may be a direction such that the first and third proximal surfaces 124A, 124C will engage with tissue or bone after the trunk is inserted therein and by natural movement of the tissue or bone. In some examples, a pullout force may be applied to the bridge 104 to further engage the first and third proximal surfaces 124A, 124C with the bone or tissue. The natural movement of the bone or tissue or the pullout force creates a first moment centered on the area of reduced stiffness adjacent each trunk, tending to rotate each trunk thereabout. The rotation of each trunk may further provide a greater holding force of the bone staple 100 in bone or tissue. The second projection 122B and the fourth projection 122D on the first and second trunks 106A, 106B, respectively, may include a second proximal surface 124B and a fourth proximal surface 124D, respectively, extending away from its respective trunk in a second direction, different from the first direction, such as inward, toward the opposite trunk. For example, the second direction may be selected such that the second and fourth proximal surfaces 124B, 124D will engage tissue or bone after each trunk is inserted therein and by natural movement of the tissue or bone. In some examples, a pullout force may be applied to the bridge 104. A slit or area of reduced cross section in each trunk adjacent the second and fourth projections 122B, 122D provide an area of weakness so that a second moment is applied to the trunk in response to natural movement of the tissue or bone and/or to a pullout force on the bridge 104. This moment causes rotation of the trunk about the area of weakness and increases the holding force of the bone staple 100.

As illustrated in the example of the bone staple 100 in FIG. 15, the first trunk 106A includes the first projection 122A disposed at an outer side of the first trunk 106A and the second projection 122B disposed at an inner side of the first trunk 106A. The first projection 122A includes the first proximal surface 124A extending away from the first trunk 106A in the first direction. With reference to FIG. 15, it will be appreciated that the first direction has an outward lateral component and a proximal component so that the first proximal surface 124A extends outwardly and proximally away from the first trunk 106A.

For example, the first direction may be selected such that the first proximal surface 124A will engage tissue or bone proximate the outer side of the first trunk 106A after being inserted therein so that a first moment is applied to the first trunk 106A in response to natural movement of the tissue or bone and/or to a pullout force on the bridge 104. The moment centers on the arm portion of lesser stiffness adjacent the first projection 122A.

In the example of FIG. 15, the first trunk 106A includes a first localized area of weakness 120A disposed proximate the second projection 122B. The second projection 122B includes the second proximal surface 124B extending away from the first trunk 106A in a second direction. The second direction is selected such that the second proximal surface 124B will engage tissue or bone proximate the inner side of the first trunk 106A when inserted therein so that a second moment is applied to the first trunk 106A in response to natural movement of the tissue or bone and/or a pullout force on the bridge 104. The moment centers around the first localized area of weakness 120A. The second moment has a direction that is generally opposite a direction of the first moment. It will be appreciated that the second direction has an inward lateral component and a proximal component so that the second proximal surface 124B extends inwardly and proximally away from the first trunk 106A. In other examples, the first arm 102A may not include the second projection 122B. In such examples, only a first moment may be applied to the first trunk 106A in response to natural movement of the tissue or bone and/or a pullout force on the bridge 104.

The second trunk 106B includes the third projection 122C disposed at an outer side of the second trunk 106B and the fourth projection 122D disposed at an inner side of the second trunk 106B. In the example of FIG. 15, the third projection 122C includes a third proximal surface 124C extending away from second trunk 106B in a third direction. With reference to FIG. 15, it will be appreciated that the third direction has an outward lateral component and a proximal component so that the third proximal surface 124C extends outwardly and proximally away from the second trunk 106B. The third direction is selected such that the third proximal surface 124C will engage tissue or bone proximate the outer side of the second trunk 106B when inserted therein so that a third moment is applied to the second trunk 106B in response to natural movement of the tissue or bone and/or a pullout force on bridge 104.

In the example of FIG. 15, the second trunk 106B includes a second localized area of weakness 120B disposed proximate the fourth projection 122D. The fourth projection 122D includes a fourth proximal surface 124D extending away from the second trunk 106B in a fourth direction. In the example of FIG. 15, the fourth direction is selected such that the second proximal surface 124B will engage tissue or bone proximate the inner side of the second trunk 106B when inserted therein so that a fourth moment is applied to the second trunk 106B in response to natural movement of the tissue or bone and/or a pullout force on the bridge 104. The fourth moment has a direction that is generally opposite a direction of the third moment. It will be appreciated that the fourth direction has an inward lateral component and a proximal component so that the fourth proximal surface 124D extends inwardly and proximally away from the second trunk 106B. In other examples, the second arm 102B may not include the fourth projection 122D. In such examples, only a first moment may be applied to the second trunk 106B in in response to natural movement of the tissue or bone and/or a pullout force on the bridge 104.

In some embodiments, the bone staple 100 includes proximal projections that extend away from or outward from the bridge 104, while the distal projections extend inward or toward the center of the bridge 104. This creates generally opposing forces in response to tension on the bridge 104 which, in combination with areas of weakness or reduced lateral extent, substantially increases the holding force of the bone staple 100 in bone as the different portions of the trunks tend to rotate in opposite directions and apply force to an opposing wall in the hole in the bone in which the bone staple 100 is positioned.

It is however, understood that other configurations of the projections are possible. In some examples, only two projections are included and they extend in different directions to cause different force responses as tension is applied to the bridge 104. Additional examples may include varying numbers of projections which produce one or more moments in each of the first and second arms 102A, 102B.

In some examples, each projection of the bone staple 100 may be clefted to form a plurality of points for greater retention in tissue or bone. In the example of FIG. 15, the first projection 122A of the first trunk 106A defines a first notch 126A that divides the first projection 122A into a first sub-projection and a second sub-projection. The second projection 122B of the second trunk 106B defines a second notch 126B. In the example of FIG. 15, the second notch 126B divides the second projection 122B into a first sub-projection and a second sub-projection. The third projection 122C of the second trunk 106B defines a third notch 126C that divides the third projection 122C into a first sub-projection and a second sub-projection. The fourth projection 122D of the second trunk 106B defines a fourth notch 126D that divides the fourth projection 122D into a first sub-projection and a second sub-projection.

With continued reference to FIG. 15, the first trunk 106A defines a first cavity 128A and the second trunk 106B defines a second cavity 128B. The first cavity 128A extends into the first trunk 106A and the second cavity 128B extends into the second trunk 106B. The first and second cavities 128A, 128B are sized to cooperate with the staple delivery insert 600 for holding and inserting the staple into tissue or bone. In summary, the staple delivery insert 600 includes longitudinally extending stakes that fit within the first and second cavities 128A, 128B to hold the bone staple 100 and push it into position in the tissue or bone as the stake abuts a portion of its respective trunk. In some examples, the cavities may extend through a portion of the length of each trunk and the distal end of the bone staple 100 is closed. Alternatively, the first cavity 128A and the second cavity 128B may extend through the entire length of the first trunk 106A and the second trunk 106B, respectively, or other portions of the bone staple 100 in some examples. In some embodiments, the first cavity 128A and the second cavity 128B each have a generally rectangular or square cross-sectional shape to cooperate with a similarly shaped cross-section on the staple delivery insert 600. However, the first cavity 128A and the second cavity 128B may have various cross-sectional shapes to cooperate with alternative staple delivery insert designs without deviating from the spirit and scope of the present disclosure.

Figure 16:
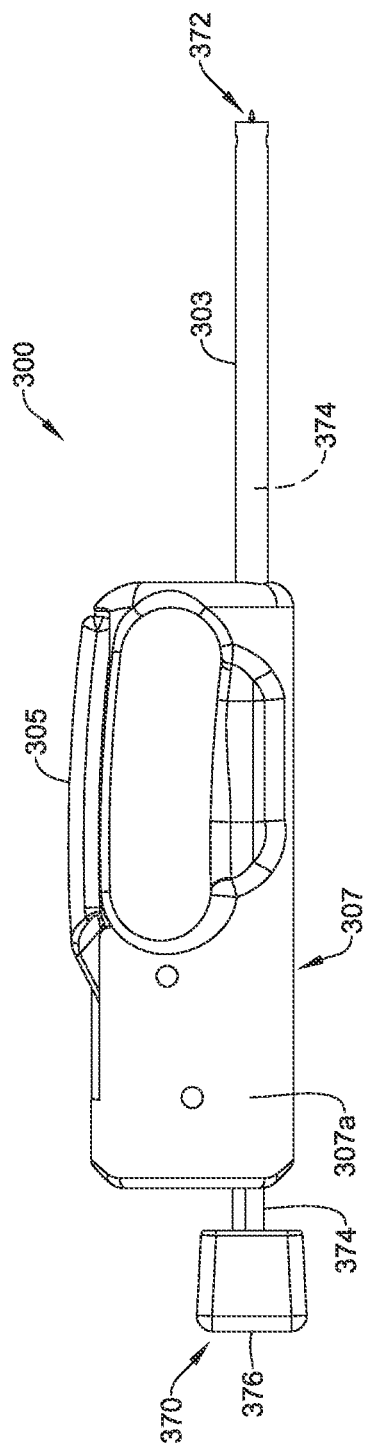
FIG. 16 is a side view illustrating aspects of an example medical device.

FIG. 16 illustrates an alternative medical device that may be used to form one or more holes within a bone (e.g., the humerus 14) of a patient to facilitate placement of the one or more bone staples 100 and/or to secure the sheet-like implant 50 to the bone. In some embodiments, the medical device may include a bone punch 370 including an elongate shaft 374 having gear teeth 375 (e.g., FIGS. 17-18) extending outwardly therefrom, a head 376 disposed at a proximal end of the elongate shaft 374, and a piercing tip 372 disposed at a distal end of the elongate shaft 374, and may be formed similarly to the bone punch 270 shown in FIG. 3 for example. In some embodiments, the bone punch 370 and/or the piercing tip 372 may include a plurality of piercing tips, two or more piercing tips, a pair of piercing tips, etc. extending distally from the distal end of the elongate shaft 374. The piercing tip 372 may be configured to be driven into the bone (e.g., the humerus 14). In some embodiments, the piercing tip 372 may be a spike, a prong, a spear, or other suitable shape. As such, the piercing tip 372 may include a sharpened distal end and/or a tapered distal portion configured to engage and/or penetrate bone.

Figure 17:
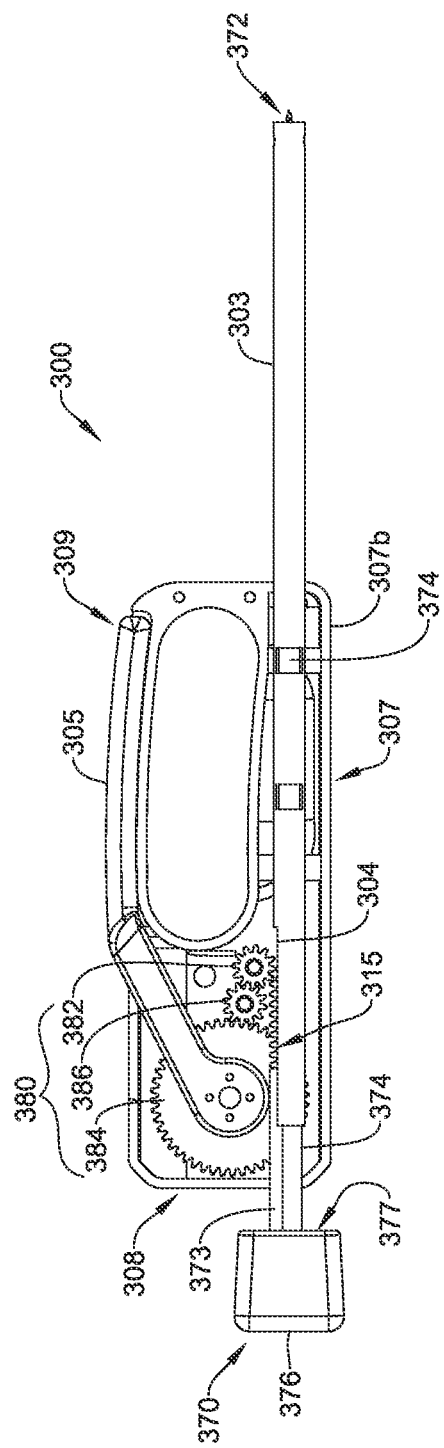
FIG. 17 illustrates aspects of the medical device of FIG. 16 with the lever in an initial position.
Figure 18:
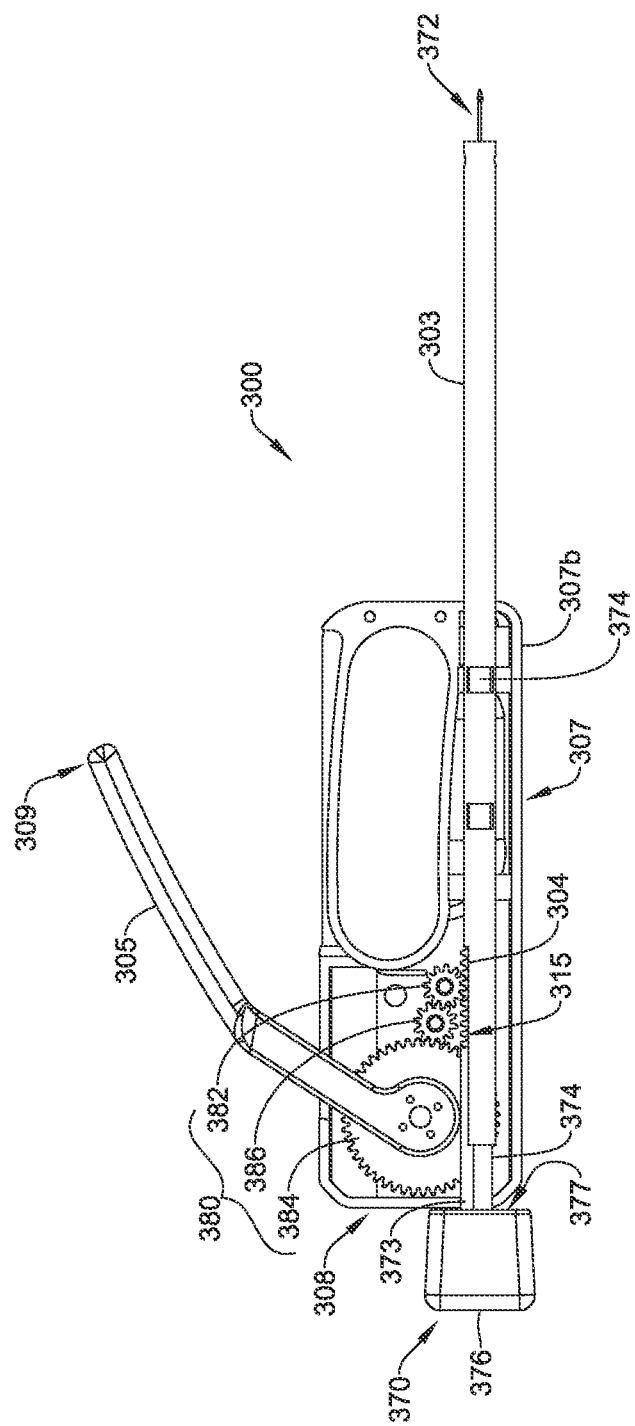
FIG. 18 illustrates aspects of the medical device of FIG. 16 with the lever in an extended position.

While a simpler version of the bone punch 370, and in particular the head 376, is illustrated in FIGS. 16-18, it is contemplated that the bone punch 370 may include some, many, and/or all of the same features shown for the bone punch 270 disclosed herein. For example, while not explicitly shown, in some embodiments, the head 376 of the bone punch 370 may include a plurality of connecting members, and each of the plurality of connecting members may include an outwardly extending protrusion, as in the bone punch 270 disclosed herein. In some embodiments, the plurality of connecting members may be fixedly attached to opposing sides of the head 376. The plurality of connecting members may extend from the head 376 distally toward the distal end of the elongate shaft 374. The plurality of connecting members may extend laterally outward from the head 376 at an oblique angle to a longitudinal axis of the bone punch 370 and/or the elongate shaft 374. In some embodiments, the plurality of connecting members may be biased laterally outward from the head 376. The bone punch 370 may function similarly to the bone punch 270 where similar elements are provided.

The head 376 of the bone punch 370 may include and/or define a distal surface 377. The distal surface 377 may be a distally facing surface and does not necessarily need to be a distalmost surface of the head 376. For example, the distal surface 377 may be disposed between a proximal end of the head 376 and the distal end of the head 376. In some embodiments, the head 376 may include one or more lateral projections. In some embodiments, the one or more lateral projections may be disposed between the plurality of connecting members and/or between the proximal end of the head 376 and the distal end of the head 376. In some embodiments, the one or more lateral projections may each and/or collectively define the distal surface 377 of the head 376.

In some embodiments, the proximal end of the elongate shaft 374 may extend into the head 376 of the bone punch 370. In some embodiments, the proximal end of the elongate shaft 374 may be fixedly attached to the head 376. In some embodiments, the elongate shaft 374 may be monolithically formed with the head 376, such as by casting, molding, or machining, for example. Other configurations are also contemplated. Similarly, a proximal end of the piercing tip 372 may extend into the distal end of the elongate shaft 374. The proximal end of the piercing tip 372 may be fixedly attached to the elongate shaft 374. In some embodiments, the piercing tip 372 may be monolithically formed with the elongate shaft 374, such as by casting, molding, or machining, for example. Other configurations are also contemplated. Some examples of suitable but non-limiting materials for the bone punch 370 and/or elements or components thereof are described below.

The medical device of FIG. 16 may comprise a handle assembly 300 including a housing 307, a lever 305 rotatably coupled to the housing 307, and a sheath 303 extending distally from the housing 307. In at least some embodiments, a proximal end of the sheath 303 may be fixedly attached to the housing 307. The sheath 303 may extend into and/or within the housing 307, such that the proximal end of the sheath 303 is disposed within a distal portion of the housing 307, and the sheath 303 extends within the housing 307 and distally from a distal end of the housing 307. Some examples of suitable but non-limiting materials for the housing 307, the lever 305, the sheath 303, and/or elements or components thereof are described below.

The housing 307 may be formed as a multi-piece structure including a first housing portion 307A, seen in FIG. 16, and a second housing portion 307B, not visible in FIG. 16.

For the purpose of illustration herein, one of the first housing portion 307A or the second housing portion 307B may be hidden from view in the figures to permit viewing of internal components and/or features thereof. The first housing portion 307A and the second housing portion 307B may be assembled together to form the housing 307. In the illustrated example(s), fasteners such as screws and nuts may be used to assemble the housing 307. However, other assembly and/or attachment means may also be used, including but not limited to snap fit, friction fit, pins, rivets, etc. In some embodiments, once the housing 307 is assembled, such assembly may be considered and/or made permanent using any known suitable means, such as but not limited to adhesives, welding, etc.

The medical device may include the bone punch 370 described herein. The bone punch 370 may be disposed within and/or extend through the sheath 303. The elongate shaft 374 may be slidably disposed within the sheath 303 in a first position when the lever 305 is in an initial position, seen in FIG. 16 for example. In some embodiments, the head 376 of the bone punch 370 may be releasably engaged with the housing 307, as described herein. In some embodiments, the head 376 of the bone punch 370 may be spaced away from a proximal surface 308 of the housing 307 in the first position. The piercing tip 372 may be positioned proximate a distal end of the sheath 303 in the first position. In some embodiments, the piercing tip 372 may be disposed within the distal end of the sheath 303 in the first position. In some embodiments, a portion of the piercing tip 372 may extend distally of the distal end of the sheath 303 in the first position to aid in positioning the medical device at a treatment site (e.g., to engage a surface of the bone). In some embodiments, less than 10% of the piercing tip 372 extends distally of the distal end of the sheath 303 in the first position. In some embodiments, less than 5% of the piercing tip 372 extends distally of the distal end of the sheath 303 in the first position.

FIG. 17 illustrates the medical device with the first housing portion 307A of the handle assembly 300 removed and the second housing portion 307B visible. The housing 307 may include a leg extending laterally from a distal portion thereof. In some embodiments, the leg may be disposed at and/or extend laterally from the distal end of the housing 307. The lever 305 may be rotatably and/or pivotably coupled to the housing 307 about an axis of rotation. In some embodiments, the handle assembly 300 may include a spring biasing the lever 305 toward the initial position.

In FIG. 17, the lever 305 is shown disposed in the initial position. In the initial position, the lever 305 may be engaged with an outer surface of the housing 307. In the initial position, the distal end 309 of the lever 305 may be substantially aligned with and/or disposed within a free end of the leg. In the initial position, the lever 305 may extend distally toward a distal end of the sheath 303 and/or the handle assembly 300 at a first angle relative to a longitudinal axis of the sheath 303. For example, the first angle may be less than about 15 degrees, less than about 10 degrees, less than about 5 degrees, about 0 degrees, or another small, oblique angle. In some embodiments, in the initial position, the lever 305 may extend toward the distal end of the sheath 303 generally parallel to a longitudinal axis of the sheath 303. In at least some embodiments, from the initial position, the lever 305 may be configured to rotate a distal end 309 of the lever 305 toward or away from the housing 307.

In FIG. 17, the bone punch 370 is shown disposed in the first position. The elongate shaft 374 of the bone punch 370 is slidably disposed within the sheath 303 of the handle assembly 300 when the lever 305 is in the initial position. The distal surface 377 of the head 376 of the bone punch 370 may be spaced apart from the proximal surface 308 of the housing 307 of the handle assembly 300 in the first position and/or when the lever 305 is in the initial position. In some embodiments, the head 376 of the bone punch 370 may be releasably engaged with the housing 307 of the handle assembly 300 in the first position and/or when the lever 305 is in the initial position. For example, a plurality of connecting members and outwardly extending protrusion(s) thereof may engage a wall of the housing 307 defining the proximal surface 308 of the housing 307. In some embodiments, the proximal surface 308 may be a proximally facing surface of the housing 307 at and/or proximate a proximal end of the housing 307. In some embodiments, the proximal surface 308 may be a proximalmost surface of the housing 307.

In the first position, the outwardly extending protrusion(s) may extend laterally outward from the head 376 and/or the longitudinal axis of the bone punch 370 and/or the elongate shaft 374 beyond a perimeter of an opening in the wall of the housing 307 within which the head 376 is disposed. Where provided, the outwardly extending protrusion(s) may prevent the head 376 and/or the bone punch 370 from being removed from the housing 307 until the plurality of connecting members are squeezed, urged, actuated, or otherwise moved inward toward the head 376, and/or the longitudinal axis of the bone punch 370 and/or the elongate shaft 374, to disengage the outwardly extending protrusion(s) from the wall of the housing 307 by translating the outwardly extending protrusion(s) inward until the outwardly extending protrusion(s) are disposed within and/or inward of the perimeter of the opening. Doing so will permit the plurality of connecting members and the outwardly extending protrusion(s) to pass through the opening in the wall of the housing 307. In the first position, the distal surface 377 of the head 376 may be spaced apart proximally from the proximal surface 308 of the wall of the housing 307.

As seen in FIG. 17, the bone punch 370 may include an elongate shaft 374 having gear teeth 375 extending outwardly therefrom. The gear teeth 375 may be disposed between a distal end of the elongate shaft 374 and the head 376. In some embodiments, the gear teeth 375 may be spaced apart from the head 376. In some embodiments, the elongate shaft 374 may include a spine 373 extending radially outward from the elongate shaft 374, wherein the spine 373 is circumferentially and/or axially aligned with the gear teeth 375. In some embodiments, the spine 373 spaces the head 376 from the gear teeth 375. In some embodiments, the gear teeth 375 may be formed from and/or cut out of the spine 373 by removing material from the spine 373 to form the gear teeth 375. In some embodiments, the spine 373 and the gear teeth 375 may be monolithically formed together. The spine 373 and the gear teeth 375 may be fixedly attached to the elongate shaft 374. In some embodiments, the spine 373 and/or the gear teeth 375 may be formed with the elongate shaft 374 as a single monolithic structure.

In some embodiments, the sheath 303 may include a slot 304 formed therein and/or through a side wall of the sheath 303 to accommodate the gear teeth 375 and/or the spine 373. The slot 304 may extend longitudinally from the proximal end of the sheath 303 in a distal direction along a proximal portion of the sheath 303. In some embodiments, the slot 304 may be oriented to face toward the lever 305.

In some embodiments, the handle assembly 300 may include a plurality of gears 380 disposed within the housing 307. At least one of the plurality of gears 380 may be configured to engage with the gear teeth 375 of the elongate shaft 374. As may be seen in FIG. 17, the gear teeth 375 of the bone punch 370 may engage at least one of the plurality of gears 380 in the first position. The plurality of gears 380 may be rotatably engaged with and/or coupled to the housing 307. The plurality of gears 380 may include a first gear 382 configured to engage the gear teeth 375 of the elongate shaft 374, a second gear 384 fixedly secured to the lever 305, and a third gear rotatably engaged with both the first gear 382 and the second gear 384. Other configurations are also contemplated.

Translation of the bone punch 370 distally within the sheath 303, and/or translation of the head 376 of the bone punch 370 distally relative to the housing 307, from the first position to a second position distal of the first position may cause the plurality of gears 380 to rotate the distal end 309 of the lever 305 away from the housing 307 and/or away from the longitudinal axis of the bone punch 370 and/or the elongate shaft 374 to an extended position, as shown in FIG. 18. In the extended position, the lever 305 may extend toward a distal end of the sheath 303 and/or the handle assembly 300 at a second angle relative to the longitudinal axis of the sheath 303. In some embodiments, the second angle may be an oblique angle. The second angle may be greater than the first angle.

As shown in FIG. 18, the distal surface 377 of the head 376 of the bone punch 370 may engage and/or abut the proximal surface 308 of the housing 307 in the second position. In the second position, the outwardly extending protrusion(s), where provided, may be spaced apart distally from the wall of the housing 307 defining the proximal surface 308. In such cases, the outwardly extending protrusion(s) may extend laterally outward from the head 376 and/or the longitudinal axis of the bone punch 370 and/or the elongate shaft 374 beyond the perimeter of the opening in the wall of the housing 307 within which the head 376 is disposed, thus preventing inadvertent removal of the bone punch 370 from the handle assembly 300.

In the second position, the piercing tip 372 may be extended from the distal end of the sheath 303 as the elongate shaft 374 is translated distally within the sheath 303. The distal end of the sheath 303 may be configured to be disposed adjacent a surface of the bone, similar to the discussion above with respect to the sheath 203 and FIG. 12. As the bone punch 370 is translated distally to the second position, the piercing tip 232 may be driven into the bone to form one or more holes in the bone. There may be a direct or indirect correlation between a rotational position of the lever 305 relative to the housing 307 and a depth of the piercing tip 372 within the bone. As the lever 305 rotates farther away from the housing 307 and/or as an angle between the lever 305 and the longitudinal axis of the sheath 303 and/or the bone punch 370 increases, the piercing tip 372 may be extended farther distally from the distal end of the sheath 303 and/or may be driven farther into the bone. A user of the medical device and/or the handle assembly 300 may be able to use the rotational position of the lever 305 relative to the housing 307 and/or the longitudinal axis of the sheath 303 and/or the bone punch 370 to indicate the depth of the piercing tip 372 within the bone, thereby providing a visual cue to the user about the status of the procedure.

Thereafter, rotation of the lever 305 from the extended position (e.g., FIG. 18) toward the initial position (e.g., FIG. 17) may generate proximal force on the bone punch 370 sufficient to overcome cortical elasticity of the bone (which is "squeezing" or "pinching" the piercing tip 372) to extract the piercing tip 372 from the bone. Accordingly, rotation of the lever 305 from the extended position (e.g., FIG. 18) toward the initial position (e.g., FIG. 17) may generate proximal translation of the bone punch 370 to thereby extract the piercing tip 372 from the bone, leaving the one or more holes formed in the bone. The plurality of gears 380 may provide a mechanical advantage in generating the force necessary to extract the piercing tip 372 from the bone, thereby reducing the force that the user needs to exert on the lever 305. Rotating the lever 305 from the extended position to the initial position may translate the bone punch 370 from the second position back to the first position. Thereafter, the bone punch 370 may be removed from the handle assembly 300 if desired, or the medical device may be removed from the treatment site.

In use, the distal end of the sheath 303 may be configured to be positioned adjacent and/or against the surface of a bone of the patient. As discussed herein, the medical device may be configured to form one or more holes within the bone. In some embodiments, the distal end of the sheath 303 may be positioned directly against the surface of the bone. In some embodiments, the distal end of the sheath 303 may be positioned against a sheet-like implant 50 that is positioned directly against the surface of the bone, similar to the sheath 203 shown in FIG. 12 for example, so that the one or more holes may also be formed in the sheet-like implant 50. As such, the presence of the sheet-like implant 50 may be considered optional.

After positioning the piercing tip 372 against the surface of the bone, the user may apply distal force to the head 376 of the bone punch 370, such as with a mallet or other tool, to drive the piercing tip 372 into the bone. In some embodiments, the sheath 303 may optionally include position retention members (e.g., position retention members 204 as seen in FIG. 12) extending distally therefrom, wherein the position retention members are configured to extend into the one or more holes formed in the bone as the piercing tip 372 is driven distally into the bone. Next, as the lever 305 is rotated toward the housing 307 to extract the piercing tip 372 from the bone, the position retention members may remain positioned within the one or more holes to maintain the position of the sheath 303 and/or the handle assembly 300 relative to the one or more holes, similar to the configuration shown in FIG. 13 for example.

In some embodiments, after disengaging the bone punch 370 from the housing 307 and/or after removing the bone punch 370 from the handle assembly 300, the user may insert a staple delivery insert 600, as depicted in FIG. 14, into the sheath 303 of the handle assembly 300. The staple delivery insert 600 may be comprised of a shaft 602, a proximal head 604, and a distal end 606. The staple delivery insert 600 may have arms 608 connected to the distal end 606 which may retain a bone staple, such as a bone staple 100, shown and described herein with respect to FIG. 15. In some examples, the arms 608 may be designed to be received into the cavities 128A, 128B of the bone staple 100 and retain the bone staple 100 with friction. Once the staple delivery insert 600 is received within the sheath 303, the user may then apply force to the proximal end of the staple delivery insert 600. The applied force may drive the arms 610 of the staple delivery insert 600, along with the bone staple 100, into the one or more holes formed in the bone. Natural movement of tissue and/or the bone, and/or a pullout force applied to the bridge of the bone staple 100, may act to secure the bone staple 100 within the bone.

The user may then remove the staple delivery insert 600 from handle assembly 300. The bone may impart a holding force on the bone staple 100 sufficient to overcome the friction force between the arms 608 of the staple delivery insert 600 and the bone staple 100 such that the staple delivery insert 600 may be removed from the bone while the bone staple 100 remains in the bone. Finally, the user may then retract the handle assembly 300 from the patient and finish the procedure.

Figure 19:
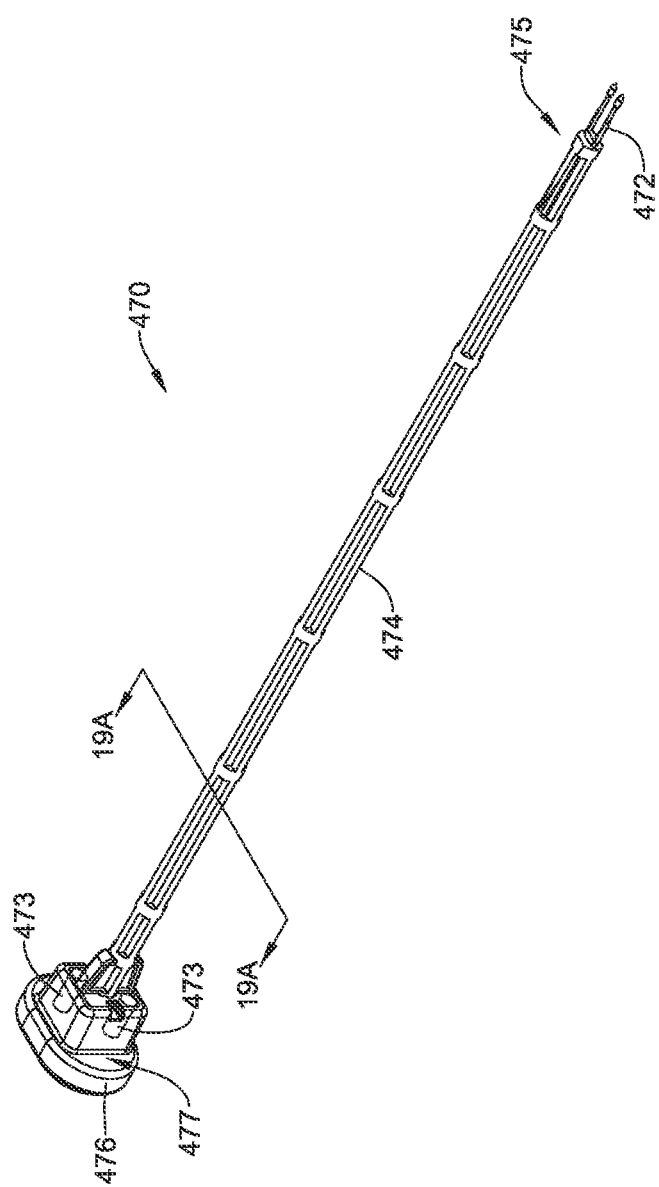
FIG. 19 is a perspective view illustrating aspects of an example bone punch.

FIG. 19 illustrates an alternative configuration of a bone punch 470 that may be used with an alternative medical device 400 (e.g., FIG. 20), described in more detail below. The bone punch 470 may include an elongate shaft 474, a head 476 disposed at a proximal end of the elongate shaft 474, and a piercing tip 472 disposed at a distal end 475 of the elongate shaft 474, as shown in FIG. 19 for example. In some embodiments, the bone punch 470 and/or the piercing tip 472 may include a plurality of piercing tips, two or more piercing tips, a pair of piercing tips, etc. extending distally from the distal end 475 of the elongate shaft 474. The piercing tip 472 may be configured to be driven into the bone (e.g., the humerus 14). In some embodiments, the piercing tip 472 may be a spike, a prong, a spear, or other suitable shape. As such, the piercing tip 472 may include a sharpened distal end and/or a tapered distal portion configured to engage and/or penetrate bone.

In some embodiments, the head 476 may include one or more lateral projections. In some embodiments, the one or more lateral projections may be disposed between a proximal end of the head 476 and a distal end of the head 476. The one or more lateral projections may each and/or collectively define a distal surface 477 of the head 476. The distal surface 477 may be a distally facing surface and does not necessarily need to be a distalmost surface of the head 476. For example, the distal surface 477 may be disposed between the proximal end of the head 476 and the distal end of the head 476. In at least some embodiments, the head 476 of the bone punch 470 may include one or more magnets 473 disposed therein. In some embodiments, the one or more magnets 473, described in more detail herein, may be fixedly attached to the head 476 using one or more of a variety of attachment means, such as but not limited to, adhesives, interference fit, friction fit, welding, co-molding, injection molding, etc. In some embodiments, the one or more magnets 473 may be embedded within the head 476. In some embodiments, at least a portion of the one or more magnets 473 may be exposed to an exterior of the head 476, such as exposed at a distally facing surface of the head 476. In some embodiments, the one or more magnets 473 may be completely embedded within the head 476 such that none of the one or more magnets 473 is exposed to the exterior of the head 476.

As shown in FIG. 19A, the head 476 may include a plurality of magnets 473 equidistantly spaced from the central longitudinal axis of the bone punch 470 such that the magnets are symmetrically arranged about the central longitudinal axis. Thus, the magnets may be arranged in the same orientation from the central longitudinal axis when the head 476 of the bone punch 470 is in any one of a plurality or rotational orientations. For example, the head 476 may include a first magnet 473 and a second magnet 473 diametrically opposite the first magnet 473, such that the first magnet 473 is in a first position and the second magnet 473 is in a second position when the head 476 of the bone punch 470 is in a first rotational orientation about the central longitudinal axis, and the first magnet 473 is in the second position and the second magnet 473 is in the first position when the head 476 of the bone punch 470 is in a second rotational orientation about the central longitudinal axis. The first rotational orientation may be 180 degrees from the second orientation, for example. In some embodiments, the proximal end of the elongate shaft 474 may extend into the head 476 of the bone punch 470. In some embodiments, the proximal end of the elongate shaft 474 may be fixedly attached to the head 476. In some embodiments, the elongate shaft 474 may be monolithically formed with the head 476, such as by casting, molding, or machining, for example. Other configurations are also contemplated. Similarly, a proximal end of the piercing tip 472 may extend into the distal end 475 of the elongate shaft 474. The proximal end of the piercing tip 472 may be fixedly attached to the elongate shaft 474. In some embodiments, the piercing tip 472 may be monolithically formed with the elongate shaft 474, such as by casting, molding, or machining, for example. Other configurations are also contemplated. Some examples of suitable but non-limiting materials for the bone punch 470 and/or elements or components thereof are described below.

Figure 20:
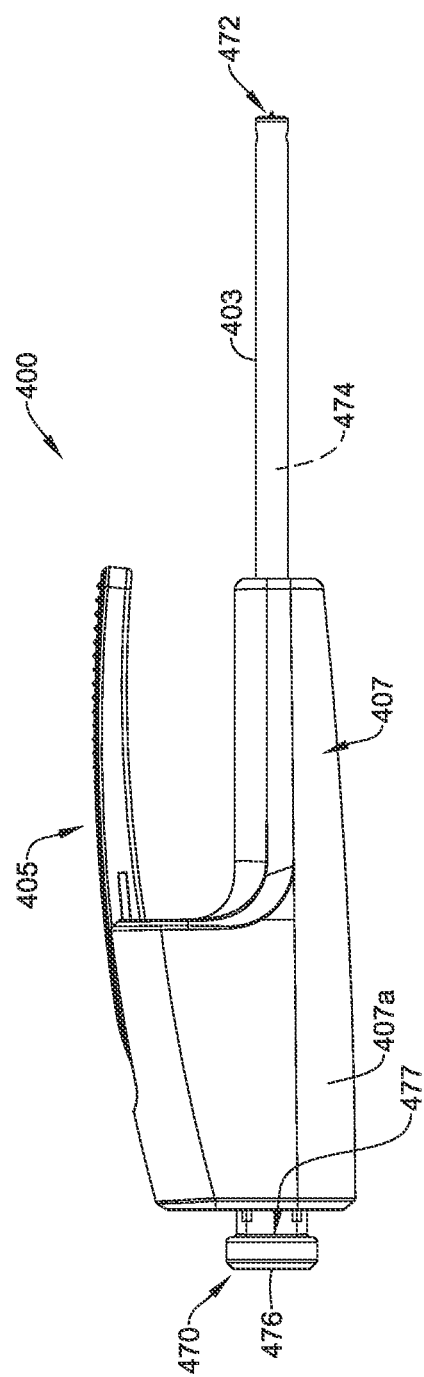
FIG. 20 is a side view illustrating aspects of an example medical device.

FIG. 20 illustrates aspects of the alternative medical device configured to form one or more holes within a bone of a patient in a side view. The medical device may comprise a handle assembly 400 including a housing 407, a lever 405 rotatably coupled to the housing 407, and a sheath 403 extending distally from the housing 407. In at least some embodiments, a proximal end of the sheath 403 may be fixedly attached to the housing 407. The sheath 403 may extend into and/or within the housing 407, such that the proximal end of the sheath 403 is disposed within the housing 407, and the sheath 403 extends distally from a distal end of the housing 407. Some examples of suitable but non-limiting materials for the housing 407, the lever 405, the sheath 403, and/or elements or components thereof are described below.

The housing 407 may be formed as a multi-piece structure including a first housing portion 407A, seen in FIG. 20, and a second housing portion 407B, not visible in FIG. 20. For the purpose of illustration herein, one of the first housing portion 407A or the second housing portion 407B may be hidden from view in the figures to permit viewing of internal components and/or features thereof. The first housing portion 407A and the second housing portion 407B may be assembled together to form the housing 407. In the illustrated example(s), fasteners such as screws and nuts may be used to assemble the housing 407. However, other assembly and/or attachment means may also be used, including but not limited to snap fit, friction fit, pins, rivets, etc. In some embodiments, once the housing 407 is assembled, such assembly may be considered and/or made permanent using any known suitable means, such as but not limited to adhesives, welding, etc.

Figure 21:
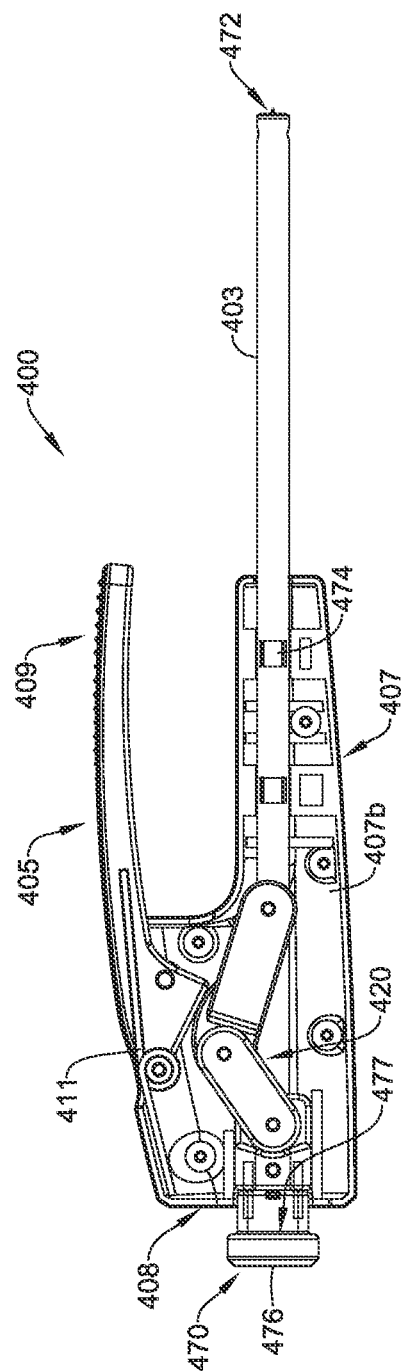
FIG. 21 illustrates aspects of the medical device of FIG. 20 with the lever in an to initial or intermediate position.

The medical device may include the bone punch 470 described herein. In some embodiments, the medical device may include the bone punch 270 and/or the bone punch 370 described herein instead of the bone punch 470. The description related to the medical device 400 will be limited to the bone punch 470 for brevity, but it will be understood that other configurations are both possible and contemplated. The bone punch 470 may be disposed within and/or extend through the sheath 403. The head 476 of the bone punch 470 may be releasably engaged with the housing 407 in a first position, as shown in FIGS. 20-21. The piercing tip 472 may be positioned proximate a distal end of the sheath 403 in the first position. In some embodiments, the piercing tip 472 may be disposed within the distal end of the sheath 403 in the first position. In some embodiments, a portion of the piercing tip 472 may extend distally of the distal end of the sheath 403 in the first position to aid in positioning the medical device at a treatment site (e.g., to engage a surface of the bone). In some embodiments, less than 50% of the piercing tip 472 extends distally of the distal end of the sheath 403 in the first position. In some embodiments, less than 40% of the piercing tip 472 extends distally of the distal end of the sheath 403 in the first position. In some embodiments, less than 30% of the piercing tip 472 extends distally of the distal end of the sheath 403 in the first position. In some embodiments, less than 20% of the piercing tip 472 extends distally of the distal end of the sheath 403 in the first position. In some embodiments, less than 10% of the piercing tip 472 extends distally of the distal end of the sheath 403 in the first position. In some embodiments, less than 5% of the piercing tip 472 extends distally of the distal end of the sheath 403 in the first position.

FIG. 21 illustrates the medical device with the first housing portion 407A of the handle assembly 400 removed and the second housing portion 407B visible. The lever 405 may be rotatably and/or pivotably coupled to the housing 407 about an axis of rotation. The handle assembly 400 may include a spring 411 biasing the lever 405 toward an initial position, such as an intermediate position. In at least some embodiments, the spring 411 may include a coiled portion disposed about and/or coaxial with the axis of rotation of the lever 405.

In FIG. 21, the lever 405 is shown disposed in the initial or intermediate position. In at least some embodiments, from the initial or intermediate position, the lever 405 may be configured to rotate a distal end 409 of the lever 405 toward or away from the housing 407. In the initial or intermediate position, the lever 405 may extend distally toward a distal end of the sheath 403 and/or the handle assembly 400 at a first angle relative to a longitudinal axis of the sheath 403. For example, the first angle may be less than about 15 degrees, less than about 10 degrees, less than about 5 degrees, about 0 degrees, or another small, oblique angle. In some embodiments, in the initial or intermediate position, the lever 405 may extend toward the distal end of the sheath 403 generally parallel to a longitudinal axis of the sheath 403.

In FIG. 21, the bone punch 470 is shown disposed in the first position. The elongate shaft 474 of the bone punch 470 is slidably disposed within the sheath 403 of the handle assembly 400 when the lever 405 is in the initial or intermediate position. In some embodiments, at least a portion of the head 476 may be configured to engage and/or pass through a wall of the housing 407 defining a proximal surface 408 of the housing 407. In some embodiments, the proximal surface 408 may be a proximally facing surface of the housing 407 at and/or proximate a proximal end of the housing 407. In some embodiments, the proximal surface 408 may be a proximalmost surface of the housing 407. In the first position, the distal surface 477 of the head 476 may be spaced apart proximally from a proximal surface 408 of the wall of the housing 407.

Figure 22:
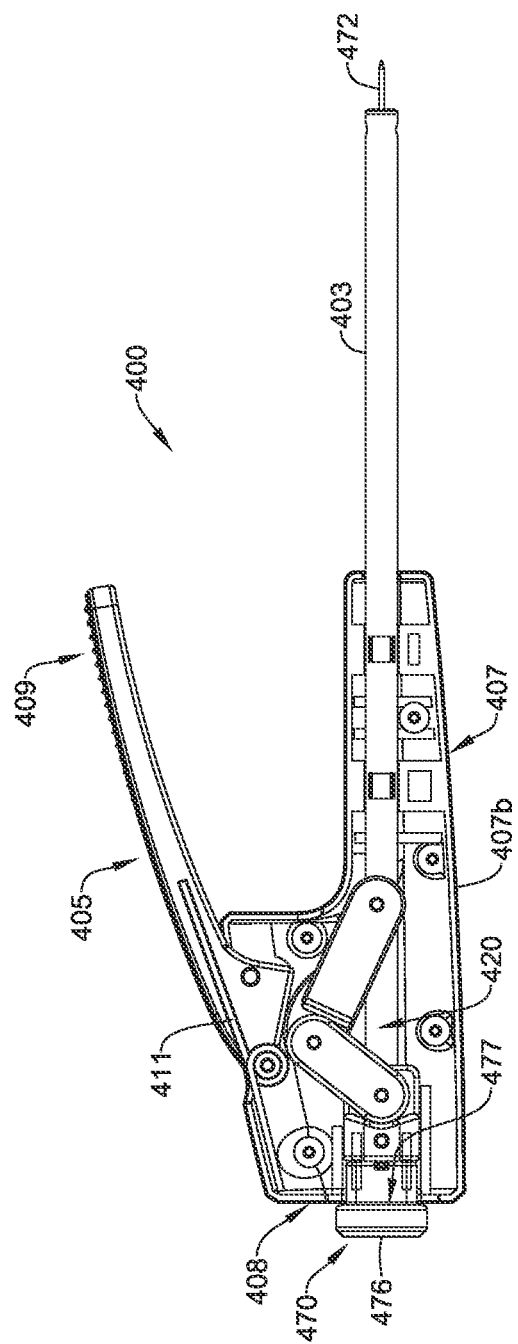
FIG. 22 illustrates aspects of the medical device of FIG. 20 with the lever in an extended position.

In some embodiments, the handle assembly 400 may include a linkage 420 disposed within the housing 407. The linkage 420 is similar in form and function to the linkage 220, except as specifically noted herein, and will be described in more detail with respect to FIG. 23. Some additional and/or functional details related to the linkage 420 may be discerned from the linkage 220 described with respect to FIGS. 8-10. As may be seen in FIG. 21, the head 476 of the bone punch 470 may engage the linkage 420 in the first position. The linkage 420 may be pivotably engaged with and/or coupled to the housing 407. The linkage 420 may include a plurality of elements that are movable and/or pivotable relative to each other. Translation of the bone punch 470 distally within the sheath 403, and/or translation of the head 476 of the bone punch 470 distally relative to the housing 407, from the first position to a second position distal of the first position may cause the linkage 420 to rotate the distal end 409 of the lever 405 away from the housing 407 and/or away from the longitudinal axis of the bone punch 470 and/or the elongate shaft 474 to an extended position, as shown in FIG. 22. In the extended position, the lever 405 may extend toward a distal end of the sheath 403 and/or the handle assembly 400 at a second angle relative to the longitudinal axis of the sheath 403. In some embodiments, the second angle may be an oblique angle. The second angle may be greater than the first angle.

As shown in FIG. 22, at least a portion of the head 476 of the bone punch 470 may be configured to pass through the opening in the wall and/or the proximal surface 408 of the housing 407 as the bone punch 470 is translated from the first position to the second position. In some embodiments, the distal surface 477 of the head 476 of the bone punch 470 may engage and/or abut the proximal surface 408 of the housing 407 in the second position. In the second position, the piercing tip 472 may be extended from the distal end of the sheath 403 as the elongate shaft 474 is translated distally within the sheath 403. The distal end of the sheath 403 may be configured to be disposed adjacent a surface of the bone. As the bone punch 470 is translated distally to the second position, the piercing tip 472 may be driven into the bone to form one or more holes in the bone. There may be a direct or indirect correlation between a rotational position of the lever 405 relative to the housing 407 and a depth of the piercing tip 472 within the bone. As the lever 405 rotates farther away from the housing 407 and/or as an angle between the lever 405 and the longitudinal axis of the sheath 403 and/or the bone punch 470 increases, the piercing tip 472 may be extended farther distally from the distal end of the sheath 403 and/or may be driven farther into the bone. A user of the medical device and/or the handle assembly 400 may be able to use the rotational position of the lever 405 relative to the housing 407 and/or the longitudinal axis of the sheath 403 and/or the bone punch 470 to indicate the depth of the piercing tip 472 within the bone, thereby providing a visual cue to the user about the status of the procedure.

Thereafter, rotation of the lever 405 from the extended position (e.g., FIG. 22) toward the initial or intermediate position (e.g., FIG. 21) may generate proximal force on the bone punch 470 sufficient to overcome cortical elasticity of the bone (which is "squeezing" or "pinching" the piercing tip 472) to extract the piercing tip 472 from the bone. Accordingly, rotation of the lever 405 from the extended position (e.g., FIG. 22) toward the initial or intermediate position (e.g., FIG. 21) may generate proximal translation of the bone punch 470 to thereby extract the piercing tip 472 from the bone, leaving the one or more holes formed in the bone. The linkage 420 may provide a mechanical advantage in generating the force necessary to extract the piercing tip 472 from the bone, thereby reducing the force that the user needs to exert on the lever 405. Rotating the lever 405 from the extended position to the initial or intermediate position may translate the bone punch 470 from the second position back to the first position. Thereafter, the bone punch 470 may be removed from the handle assembly 400 if desired, or the medical device may be removed from the treatment site.

Figure 23:
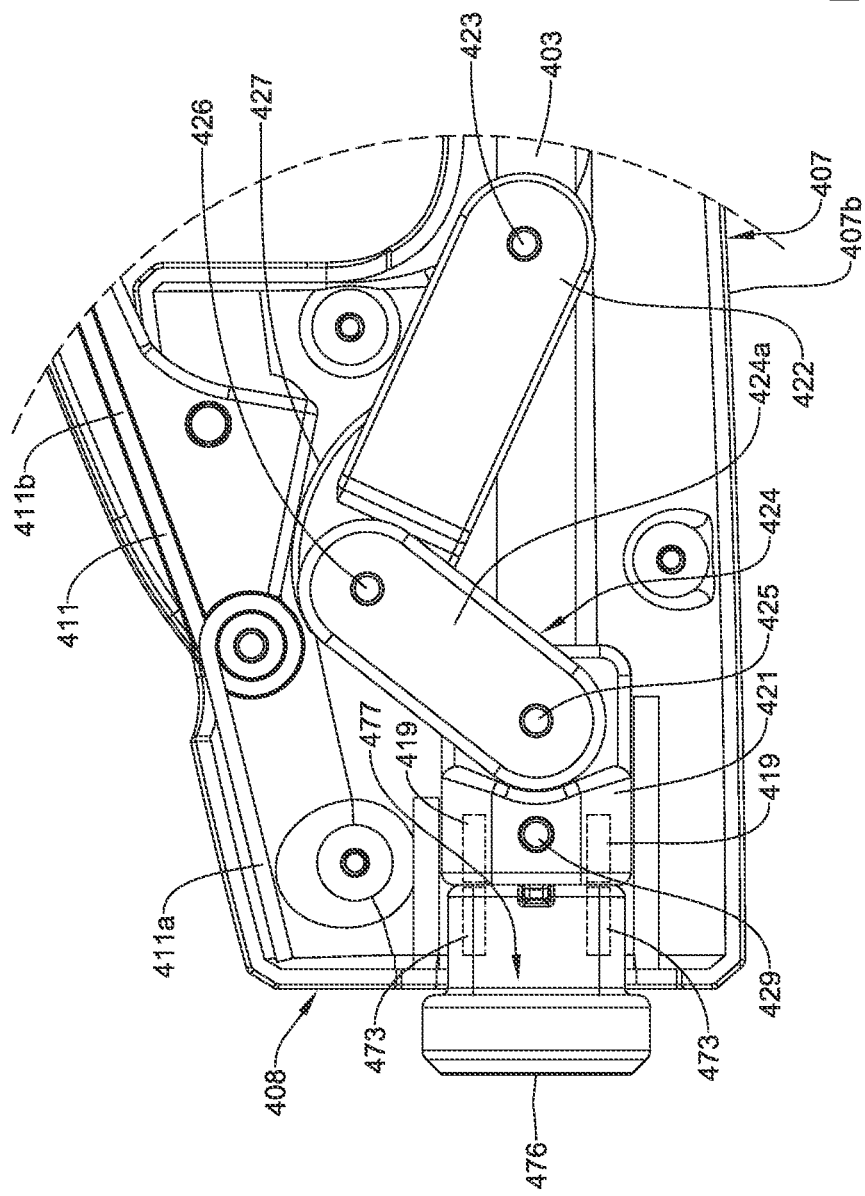
FIG. 23 is a detailed view illustrating aspects of the medical device of FIG. 20 with the lever in the extended position of FIG. 22.

FIG. 23 is a detailed view of a portion of the medical device of FIG. 22, wherein the bone punch 470 is disposed in the second position and the lever 405 is disposed in the extended position. The linkage 420 may include an ejector block 421 slidably disposed within the housing 407. The ejector block 421 may include one or more pins 429 configured to engage the housing 407 and/or configured to slide longitudinally and/or axially within a channel formed in the housing 407. In some embodiments, the ejector block 421 may be configured to slide longitudinally and/or axially within a channel formed in the housing 407. In some embodiments, the ejector block 421 may be configured to slide parallel to the longitudinal axis of the sheath 403 and/or the longitudinal axis of the bone punch 470 and/or the elongate shaft 474. In some embodiments, the sheath 403 may extend through and/or may pass through the ejector block 421. As such, the ejector block 421 may be slidably disposed about the sheath 403. Since the elongate shaft 474 may be slidably disposed within the sheath 403, the elongate shaft 474 may also extend through the ejector block 421. The head 476 of the bone punch 470 may be releasably coupled to the ejector block 421 in the first position (e.g., FIG. 21) and/or when the lever 405 is in the initial or intermediate position. During distal translation of the bone punch 470 from the first position to the second position (e.g., FIG. 22), the head 476 of the bone punch 470 may push, urge, or otherwise translate the ejector block 421 distally within the housing 407, while remaining releasably coupled to the ejector block 421, thereby actuating the linkage 420 and causing the linkage 420 to rotate the distal end 409 of the lever 405 away from the housing 407 to the extended position.

In at least some embodiments, the ejector block 421 may include one or more magnets 419 disposed therein. In some embodiments, the one or more magnets 419, described in more detail herein, may be fixedly attached to the ejector block 421 using one or more of a variety of attachment means, such as but not limited to, adhesives, interference fit, friction fit, welding, co-molding, injection molding, etc. In some embodiments, the one or more magnets 419 may be embedded within the ejector block 421. In some embodiments, at least a portion of the one or more magnets 419 may be exposed to an exterior of the ejector block 421, such as exposed at a proximally facing surface of the ejector block 421 facing or juxtaposed with a distally facing surface of the head 476. In some embodiments, the one or more magnets 419 may be completely embedded within the ejector block 421 such that none of the one or more magnets 419 is exposed to the exterior of the ejector block 421.

In some embodiments, the head 476 of the bone punch 470 may be magnetically coupled to the ejector block 421. As discussed herein, in some embodiments, the head 476 of the bone punch 470 may include one or more magnets 473 disposed therein and the ejector block 421 may include one or more magnets 419 disposed therein. The one or more magnets 473 of the head 476 of the bone punch 470 may be opposite polarity to the one or more magnets 419 of the ejector block 421, so as to exert an attractive magnetic force on each other to releasably couple the head 476 of the bone punch 470 to the ejector block 421.

In some embodiments, the one or more magnets 419 in the ejector block 421 may instead be a magnetic material (e.g., a ferrous metal, etc.). As such, the head 476 of the bone punch 470 may include one or more magnets 473 disposed therein and the ejector block 421 may include the magnetic material disposed therein opposite the one or more magnets 473 of the head 476 so as to exert an attractive magnetic force on each other to releasably couple the head 476 of the bone punch 470 to the ejector block 421.

In some embodiments, the one or more magnets 473 in the head 476 of the bone punch 470 may instead be a magnetic material (e.g., a ferrous metal or other material that is magnetically attracted to a magnet,etc.). As such, the ejector block 421 may include one or more magnets 419 disposed therein and the head 476 of the bone punch 470 may include the magnetic material disposed therein opposite the one or more magnets 419 of the ejector block 421 so as to exert an attractive magnetic force on each other to releasably couple the head 476 of the bone punch 470 to the ejector block 421.

In at least some embodiments, the linkage 420 may further include a distal link 422 pivotably engaged with the housing 407 at a distal pivot point 423, and a middle link 424 pivotably engaged with the ejector block 421 at a proximal pivot point 425. In some embodiments, the middle link 424 may include a first middle link 424A and a second middle link 424B (not shown). In some embodiments, a proximal portion of the distal link 422 may be disposed between the first middle link 424A and the second middle link 424B. In some embodiments, a distal portion of the distal link 422 may comprise a pair of opposing legs extending on opposite sides of the sheath 403. One leg of the pair of opposing legs may be configured to engage the first housing portion 407A, and one leg (e.g., the opposite leg) of the pair of opposing legs may be configured to engage the second housing portion 407B.

The distal link 422 may be pivotably engaged with the middle link 424 at an intermediate pivot point 426 between the distal pivot point 423 and the proximal pivot point 425. The distal pivot point 423 may be axially and/or longitudinally fixed relative to the housing 407. As such, when the head 476 of the bone punch 470 is translated distally to slide the ejector block 421 distally within the housing 407, a proximal end of the distal link 422 and a distal end of the middle link 424 may be translated laterally relative to the longitudinal axis of the sheath 403, the bone punch 470, and/or the elongate shaft 474 by pivoting relative to each other at the intermediate pivot point 426 as a proximal end of the middle link 424 is translated distally and/or longitudinally toward a distal end of the distal link 422 and/or the distal pivot point 423. In some embodiments, the proximal pivot point 425, the intermediate pivot point 426, and/or the distal pivot point 423 may include and/or be defined by one or more pins, shafts, or other elements. Some examples of suitable but non-limiting materials for the ejector block 421, the distal link 422, the middle link 424, and/or elements or components thereof are described below.

The distal link 422 may include a cam surface 427 configured to engage a corresponding surface of the lever 405, wherein the corresponding surface of the lever 405 faces toward the housing 407, the distal link 422, and/or the longitudinal axis of the sheath 403, the bone punch 470, and/or the elongate shaft 474. In some embodiments, the cam surface 427 may be a curved surface. In some embodiments, the cam surface 427 may be a convex surface. In some embodiments, the corresponding surface of the lever 405 may be a curved surface. In some embodiments, the corresponding surface of the lever 405 may be a convex surface. In some embodiments, the corresponding surface of the lever 405 may be a concave surface. In some embodiments, the corresponding surface of the lever 405 may be a complex and/or an irregular surface having both concave and convex portions. Other configurations are also contemplated.

As discussed above, the handle assembly 400 may include a spring 411 disposed within the housing 407. The spring 411 may include a first arm portion 411A extending proximally from the coiled portion and configured to engage the housing 407. In at least some embodiments, the first arm portion 411A may be configured to engage the first housing portion 407A (not shown). The spring 411 may include a second arm portion 411B extending distally from the coiled portion and configured to engage the lever 405.

For example, the lever 405 may include a slot formed therein configured to receive the second arm portion 411B. As mentioned above, the spring 411 and the lever 405 may function similar to and/or the same as the spring 211 and the lever 205 described with respect to FIGS. 8-10.

Figure 24:
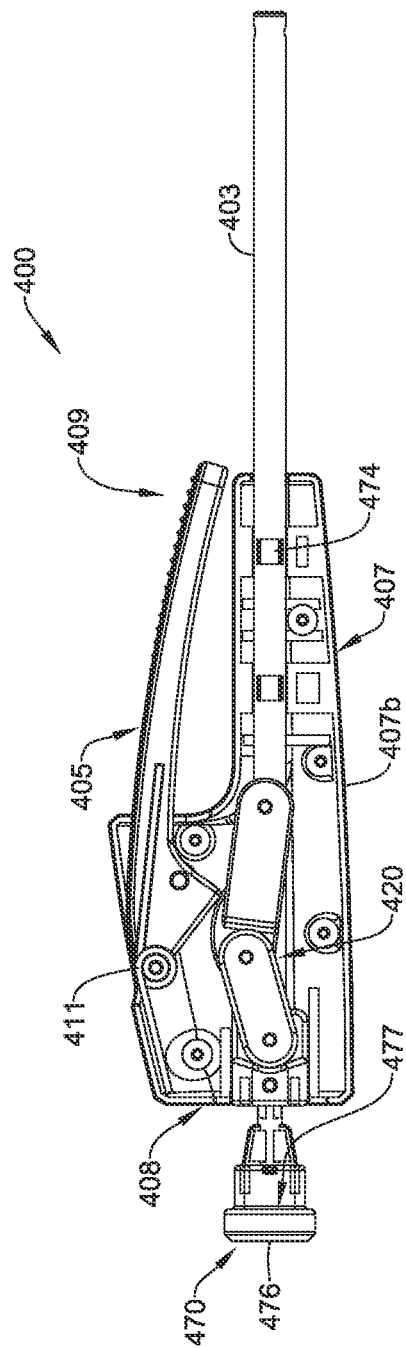
FIG. 24 illustrates aspects of the medical device of FIG. 20 with the lever in a disengagement position.

In some embodiments, the lever 405 may be rotated toward the housing 407 and/or the longitudinal axis of the sheath 403, the bone punch 470, and/or the elongate shaft 474 toward a disengagement position, shown in FIG. 24, to aid in ejecting the bone punch 470 from the handle assembly 400. However, it will be appreciated that moving and/or translating the lever 405 toward and/or to the disengagement position is not strictly to necessary to eject the bone punch 470 from the handle assembly 400. In at least some embodiments, after the piercing tip 472 has been extracted from the bone, sufficient manual retraction force may be applied to the head 476 of the bone punch 470 to overcome the magnetic force coupling the head 476 of the bone punch 470 to the ejector block 421 and thereby separate the head 476 of the bone punch 470 from the ejector block 421, thus permitting removal of the bone punch 470 from the handle assembly 400.

Figure 25:
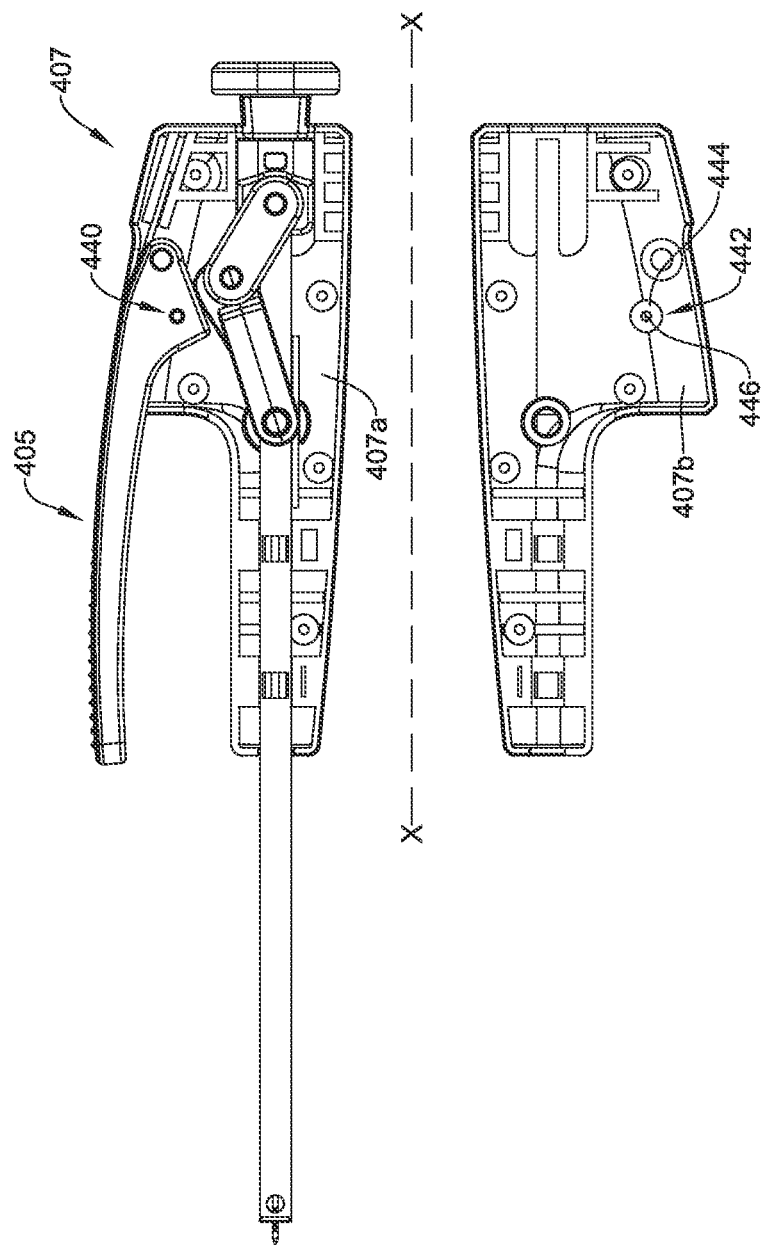
FIG. 25 illustrates selected aspects of an example configuration of the medical device of FIG. 20.

FIG. 25 illustrates an example configuration of the housing 407, wherein the housing 407 may include and/or may be formed as a multi-piece structure including a first housing portion 407A and a second housing portion 407B as described herein. For the purpose of illustration, the second housing portion 407B is rotated about the axis X-X to permit viewing of internal components and/or features of the housing 407 and external features of the lever 405. In the illustrated example, the lever 405 may include a protrusion 440 extending laterally from the lever 405 on a left side of the lever 405, as viewed proximally to distally. In some embodiments, the protrusion 440 may be and/or may include a spring-loaded ball plunger disposed within a cavity formed in the lever 405, wherein a ball of the spring-loaded ball plunger is biased toward an extended position in which the ball protrudes laterally from an outside surface of the lever 405.

The second housing portion 407B may include a receiving feature 442 configured to align with and/or receive the ball of the protrusion 440 therein when the lever 405 is disposed in the initial and/or intermediate position. In the illustrated example, the receiving feature 442 includes an annular shoulder 444 extending inward from the second housing portion 407B, wherein the annular shoulder 444 defines a central aperture 446 configured to receive the ball of the protrusion 440 when the lever 405 is disposed in the initial and/or intermediate position, thereby aiding in maintaining the lever 405 in the initial and/or intermediate position by preventing free and/or accidental movement of the lever 405 away from the initial and/or intermediate position. In some embodiments, when the lever 405 is disposed in the extended position, a position of the ball of the protrusion 440 is shifted in a direction away from the longitudinal axis of the sheath 403 and the ball of the protrusion 440 extends outside of and/or alongside the annular shoulder 444 of the receiving feature 442 above the receiving feature 442 (as viewed from the side) on an opposite side of the receiving feature 442 relative to the longitudinal axis of the sheath 403, thereby aiding in maintaining the lever 405 in the extended position by preventing free and/or accidental movement of the lever 405 away from the extended position. In some embodiments, when the lever 405 is disposed in the disengagement position, the position of the ball of the protrusion 440 is shifted in a direction toward the longitudinal axis of the sheath 403 and the ball of the protrusion 440 extends outside of and/or alongside the annular shoulder 444 of the receiving feature 442 above the receiving feature 442 (as viewed from the side) on a same side of the receiving feature 442 as the longitudinal axis of the sheath 403, thereby aiding in maintaining the lever 405 in the disengagement position by preventing free and/or accidental movement of the lever 405 away from the disengagement position. It will be appreciated that application of a sufficient force to the lever 405 may overcome any resistance to movement provided by the ball of the protrusion 440 being engaged with the receiving feature 442 such that the lever 405 may be selectively and intentionally moved between the above-referenced positions (e.g., the initial and/or intermediate position, the extended position, and the disengagement position).

Figure 26:
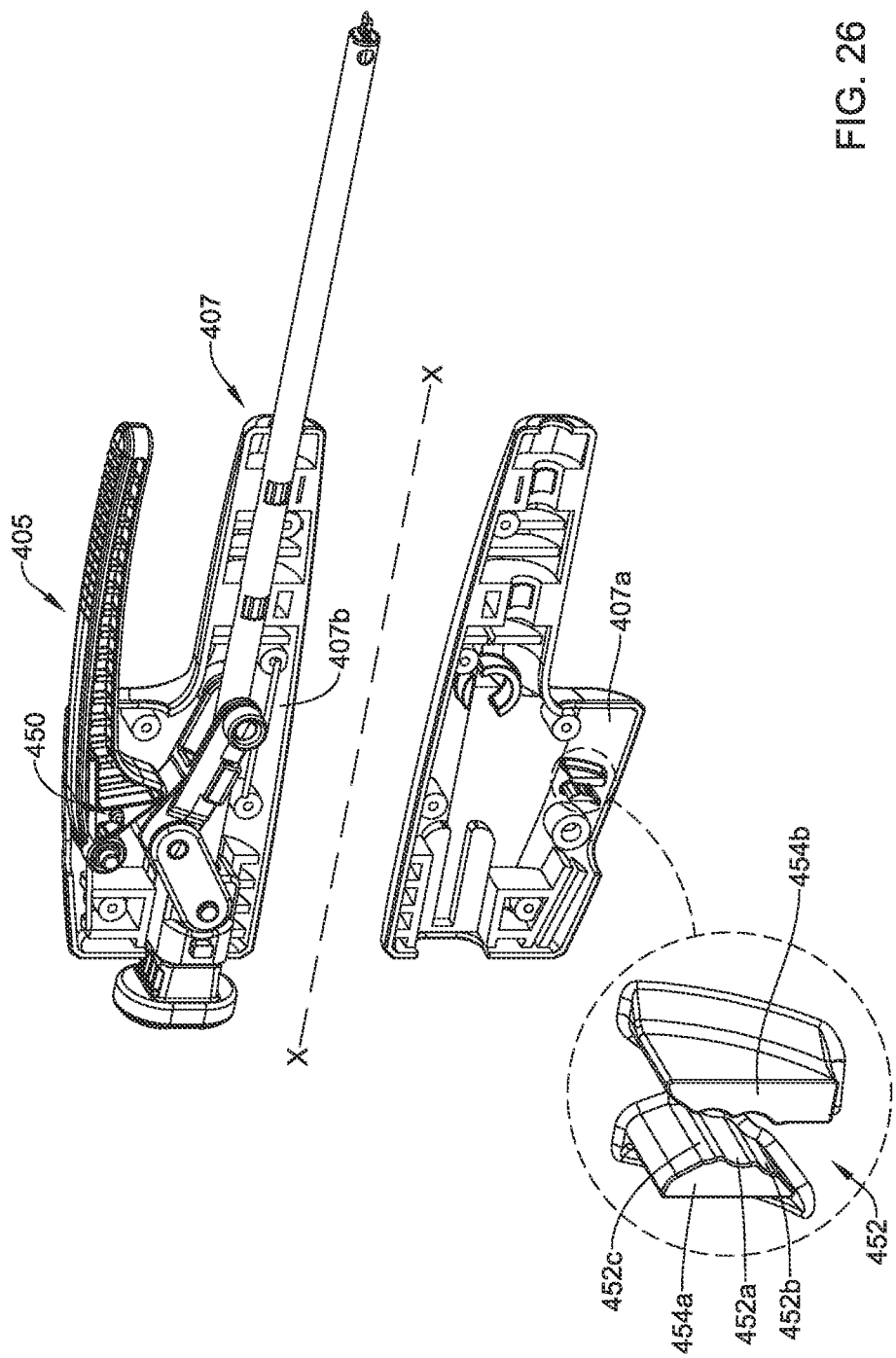
FIG. 26 illustrates selected aspects of an example configuration of the medical device of FIG. 20.

FIG. 26 illustrates an example configuration of the housing 407, wherein the housing 407 may include and/or may be formed as a multi-piece structure including a first housing portion 407A and a second housing portion 407B as described herein. For the purpose of illustration, the second housing portion 407B is rotated about the axis X-X to permit viewing of internal components and/or features of the housing 407 and external features of the lever 405. In the illustrated example, the lever 405 may include a protrusion 450 extending laterally from the lever 405 on a right side of the lever 405, as viewed proximally to distally. In some embodiments, the protrusion 450 may be and/or may include a fixed projection that protrudes laterally from an outside surface of the lever 405.

The first housing portion 407A may include a receiving feature 452 configured to align with and/or receive the protrusion 450 therein. In at least some embodiments, the receiving feature 452 may include a plurality of recesses including a first recess 452a, a second recess 452b, and a third recess 452c. Fewer and/or additional recesses and/or other configurations are also contemplated. In the illustrated example, the receiving feature 452 includes a proximal shoulder 454A and a distal shoulder 454B extending inward from the first housing portion 407A, wherein the proximal shoulder 454A and the distal shoulder 454B collectively define the first recess 452a, the second recess 452b, and the third recess 452c, which recesses are configured to receive the protrusion 450 in the initial and/or intermediate position, the extended position, and the disengagement position, respectively. The receiving feature 452 and/or the plurality of recesses may be configured to aid in maintaining the lever 405 in one or more of the above-referenced positions (e.g., the initial and/or intermediate position, the extended position, and the disengagement position) by substantially preventing free and/or accidental movement of the lever 405.

In some embodiments, the when the lever 405 is positioned in the initial and/or intermediate position, a portion of the protrusion 450 is disposed within and engaged with the first recess 452a, thereby aiding in maintaining the lever 405 in the initial and/or intermediate position by preventing free and/or accidental movement of the lever 405 away from the initial and/or intermediate position. In some embodiments, when the lever 405 is disposed in the extended position, the position of the protrusion 450 is shifted in a direction away from the longitudinal axis of the sheath 403 and the protrusion 450 is disposed within and engaged with the second recess 452b, thereby aiding in maintaining the lever 405 in the extended position by preventing free and/or accidental movement of the lever 405 away from the extended position. In some embodiments, when the lever 405 is disposed in the disengagement position, the position of the protrusion 450 is shifted in a direction toward the longitudinal axis of the sheath 403 and the protrusion 450 is disposed within and/or engaged with the third recess 452c, thereby aiding in maintaining the lever 405 in the disengagement position by preventing free and/or accidental movement of the lever 405 away from the disengagement position. It will be appreciated that application of a sufficient force to the lever 405 may overcome any resistance to movement provided by the protrusion 450 being engaged with the receiving feature 452 and/or the first recess 452a, the second recess 452b, and/or the third recess 452c, such that the lever 405 may be selectively and intentionally moved between the above-referenced positions (e.g., the initial and/or intermediate position, the extended position, and the disengagement position).

Figure 27:
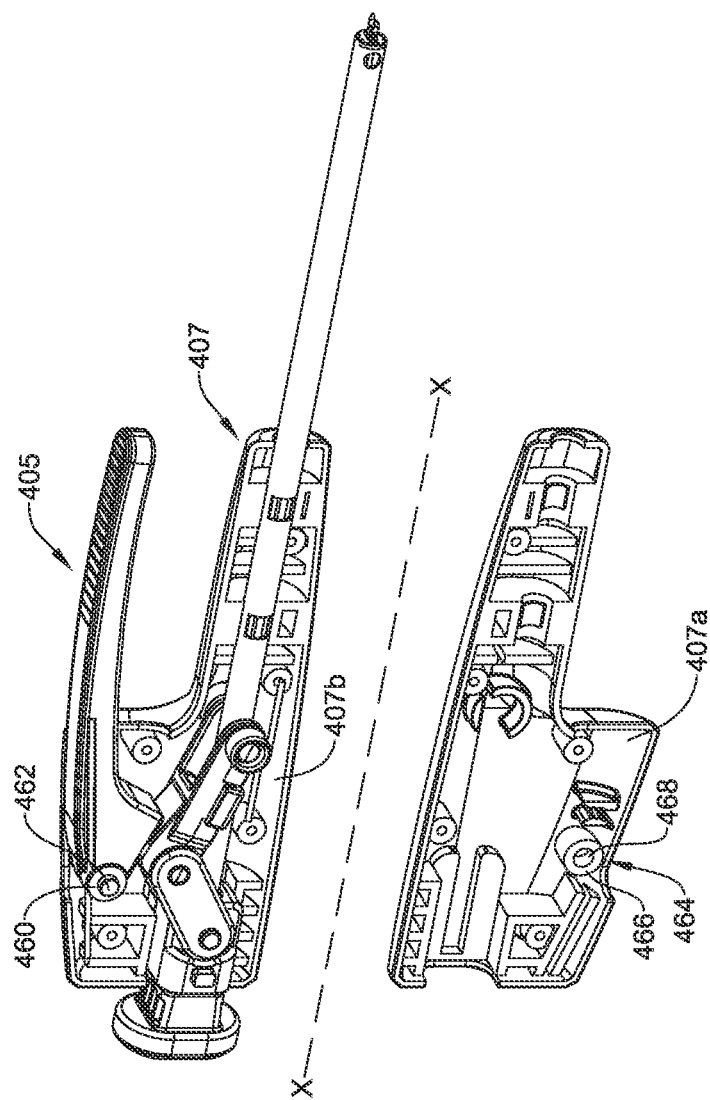
FIG. 27 illustrates selected aspects of an example configuration of the medical device of FIG. 20.

FIG. 27 illustrates an example configuration of the housing 407, wherein the housing 407 may include and/or may be formed as a multi-piece structure including a first housing portion 407A and a second housing portion 407B as described herein. For the purpose of illustration, the first housing portion 407A is rotated about the axis X-X to permit viewing of internal components and/or features of the housing 407 and external features of the lever 405. In the illustrated example, the lever 405 may include a polymeric washer 460 disposed over and/or around a protrusion 462 extending laterally from the lever 405 on a right side of the lever 405, as viewed proximally to distally. In some embodiments, the polymeric washer 460 may be disposed over and/or around a protrusion extending laterally from the lever 405 on a left side of the lever 405, as viewed proximally to distally. In some embodiments, polymeric washers 460 may be disposed over and/or around protrusions extending laterally from the lever 405 on both the left and right sides of the lever 405. The protrusion 462 (or protrusions) may correspond to and/or may be aligned and/or coaxial with a pivot axis of the lever 405 relative to the housing 407. In some embodiments, the polymeric washer 460 may be formed from and/or may include a material having a high coefficient of friction with respect to the housing 407 and/or the lever 405. For example, the polymeric washer 460 may be formed from a rubber material, a urethane material, a silicone material, or another material that will increase friction between the lever 405 and the housing 407 as the lever 405 is rotated about the pivot axis compared to when the polymeric washer 460 is absent (e.g., not present).

The first housing portion 407A and/or the second housing portion 407B may each include a receiving feature 464 configured to receive the protrusion 462. In the illustrated example, the receiving feature 464 includes an annular shoulder 466 extending inward from the second housing portion 407B, wherein the annular shoulder 466 defines a central aperture 468 configured to receive the protrusion 462. The polymeric washer 460 may be configured to matingly and/or frictionally engage both the lever 405 and the annular shoulder 466 when the protrusion 462 is disposed within the central aperture 468. In some embodiments, the polymeric washer 460 may be sandwiched, compressed, and/or pinched between the lever 405 and the housing 407 (e.g., the first housing portion 407A and/or the second housing portion 407B). Such a configuration will increase friction between the lever 405 and the housing 407. As such, when the lever 405 is disposed in the initial and/or intermediate position, the polymeric washer 460 may aid in maintaining the lever 405 in the initial and/or intermediate position by preventing free and/or accidental movement of the lever 405 away from the initial and/or intermediate position. In some embodiments, when the lever 405 is disposed in the extended position, the polymeric washer 460 may aid in maintaining the lever 405 in the extended position by preventing free and/or accidental movement of the lever 405 away from the extended position. In some embodiments, when the lever 405 is disposed in the disengagement position, the polymeric washer 460 may aid in maintaining the lever 405 in the disengagement position by preventing free and/or accidental movement of the lever 405 away from the disengagement position. The materials that can be used for the various components of the medical device(s) and the various elements thereof disclosed herein may include those commonly associated with medical devices. For simplicity purposes, the following discussion refers to the apparatus. However, this is not intended to limit the devices and methods described herein, as the discussion may be applied to other elements, members, components, or devices disclosed herein, such as, but not limited to, the medical device, the housing assembly, the bone punch, the bone staple, and/or elements or components thereof.

In some embodiments, the apparatus, and/or components thereof, may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304 L, and 316 LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the apparatus, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the apparatus in determining its location. Some examples of radiopaque materials can include, but are not limited to, gold, to platinum, palladium, tantalum, tungsten alloy, polymer material loaded with a radiopaque filler, and the like. Additionally, other radiopaque marker bands and/or coils may also be incorporated into the design of the apparatus to achieve the same result.

In some embodiments, a degree of Magnetic Resonance Imaging (MRI) compatibility is imparted into the apparatus and/or other elements disclosed herein. For example, the apparatus, and/or components or portions thereof, may be made of a material that does not substantially distort the image and create substantial artifacts (e.g., gaps in the image). Certain ferromagnetic materials, for example, may not be suitable because they may create artifacts in an MRI image. The apparatus, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the apparatus and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device configured to form one or more holes within a bone of a patient, comprising:
   a handle assembly including a housing, a lever rotatably coupled to the housing between an initial position and an extended position, and a sheath extending distally from the housing; and
   a bone punch including an elongate shaft, a head at a proximal end of the elongate shaft, and a piercing tip at a distal end of the elongate shaft, wherein the piercing tip is configured to be driven into the bone;
   wherein the elongate shaft is slidably disposed within the sheath in a first position when the lever is in the initial position;
   wherein the handle assembly includes a linkage disposed within the housing, the linkage including an ejector block slidably disposed within the housing;
   wherein the head of the bone punch is releasably coupled to the ejector block in the first position, and distal translation of the bone punch from the first position to a second position causes the linkage to rotate a distal end of the lever away from the housing to the extended position; and
   wherein rotation of the lever from the extended position toward a longitudinal axis of the bone punch when the bone punch is in the second position generates proximal translation of the bone punch to extract the piercing tip from the bone.

2. The medical device of claim 1, wherein the head of the bone punch is magnetically coupled to the ejector block.

3. The medical device of claim 2, wherein the head of the bone punch includes one or more magnets disposed therein and the ejector block includes a magnetic material disposed therein opposite the one or more magnets.

4. The medical device of claim 2, wherein the ejector block includes one or more magnets disposed therein and the head of the bone punch includes a magnetic material disposed therein opposite the one or more magnets.

5. The medical device of claim 2, wherein the head of the bone punch includes one or more magnets disposed therein and the ejector block includes one or more magnets disposed therein opposite the one or more magnets disposed in the head of the bone punch.

6. The medical device of claim 1, wherein distal translation of the head of the bone punch from the first position to the second position translates the ejector block distally within the housing.

7. A medical device configured to form one or more holes within a bone of a patient, comprising:
   a handle assembly including a housing, a lever rotatably coupled to the housing between an initial position and an extended position, and a sheath extending distally from the housing; and
   a bone punch including an elongate shaft, a head at a proximal end of the elongate shaft, and a piercing tip at a distal end of the elongate shaft, wherein the piercing tip is configured to be driven into the bone;
   wherein the elongate shaft is slidably disposed within the sheath in a first position when the lever is in the initial position;
   wherein translation of the bone punch distally within the sheath from the first position to a second position causes a distal end of the lever to rotate away from the housing to the extended position; and
   wherein translation of the bone punch distally within the sheath from the first position to the second position causes the distal end of the lever to rotate away from a longitudinal axis of the bone punch.

8. The medical device of claim 7, wherein the head of the bone punch is releasably engaged with the housing in the first position.

9. The medical device of claim 8, wherein a distal surface of the head of the bone punch engages a proximal surface of the housing in the second position.

10. The medical device of claim 7, wherein less than 40% of the piercing tip extends distally of the sheath in the first position.

11. The medical device of claim 7, wherein a distal end of the sheath is configured to be disposed adjacent a surface of the bone; and
    wherein a rotational position of the lever relative to the housing indicates a depth of the piercing tip within the bone.

12. The medical device of claim 7, wherein rotation of the lever from the extended position toward the initial position generates proximal translation of the bone punch to extract the piercing tip from the bone.

13. A medical device configured to form one or more holes within a bone of a patient, comprising:
    a handle assembly including a housing, a lever rotatably coupled to the housing between an initial position and an extended position, and a sheath extending distally from the housing; and
    a bone punch including an elongate shaft, a head at a proximal end of the elongate shaft, and a piercing tip at a distal end of the elongate shaft, wherein the piercing tip is configured to be driven into the bone;

wherein the elongate shaft is slidably disposed within the sheath in a first position when the lever is in the initial position;

wherein the handle assembly includes a linkage disposed within the housing;

wherein the head of the bone punch engages the linkage in the first position and distal translation of the bone punch from the first position to a second position causes the linkage to rotate a distal end of the lever away from the housing to the extended position;

wherein rotation of the lever toward a longitudinal axis of the bone punch when the bone punch is in the second position actuates the linkage to translate the head of the bone punch proximally to extract the piercing tip from the bone.

14. The medical device of claim 13, wherein the linkage includes an ejector block slidably disposed within the housing.

15. The medical device of claim 14, wherein the linkage further includes a distal link pivotably engaged with the housing at a distal pivot point and a middle link pivotably engaged with the ejector block at a proximal pivot point;

wherein the distal link is pivotably engaged with the middle link at an intermediate pivot point between the distal pivot point and the proximal pivot point.

16. The medical device of claim 14, wherein distal translation of the head of the bone punch from the first position to the second position translates the ejector block distally within the housing.

17. A medical device configured to form one or more holes within a bone of a patient, comprising:

a handle assembly including a housing, a lever rotatably coupled to the housing between an initial position and an extended position, and a sheath extending distally from the housing; and a bone punch including an elongate shaft having gear teeth extending outwardly therefrom, a head at a proximal end of the elongate shaft, and a piercing tip at a distal end of the elongate shaft, wherein the piercing tip is configured to be driven into the bone;

wherein the elongate shaft is slidably disposed within the sheath in a first position when the lever is in the initial position;

wherein the handle assembly includes a plurality of gears disposed within the housing, at least one of the plurality of gears being configured to engage with the gear teeth of the elongate shaft;

wherein the head of the bone punch is spaced away from a proximal surface of the housing in the first position and distal translation of the bone punch from the first position to a second position causes the plurality of gears to rotate a distal end of the lever away from the housing to the extended position.

18. The medical device of claim 17, wherein in the initial position, the lever is engaged with an outer surface of the housing.

19. The medical device of claim 17, wherein:

in the initial position, the lever extends toward a distal end of the sheath generally parallel to a longitudinal axis of the sheath;

in the extended position, the lever extends toward a distal end of the sheath at an oblique angle to the sheath.

* * * * *